United States Patent
Zhou et al.

(10) Patent No.: US 10,450,331 B2
(45) Date of Patent: Oct. 22, 2019

(54) FUNCTIONALIZED CYANOSILANE AND SYNTHESIS METHOD AND USE THEREOF

(71) Applicant: EAST CHINA NORMAL UNIVERSITY, Shanghai (CN)

(72) Inventors: Jian Zhou, Shanghai (CN); Xingping Zeng, Shanghai (CN)

(73) Assignee: EAST CHINA NORMAL UNIVERSITY, Shanghai (CN)

( * ) Notice: Subject to any disclaimer, the term of this patent is extended or adjusted under 35 U.S.C. 154(b) by 0 days.

(21) Appl. No.: 15/876,464

(22) Filed: Jan. 22, 2018

(65) Prior Publication Data

US 2018/0141964 A1     May 24, 2018

Related U.S. Application Data

(63) Continuation-in-part of application No. PCT/CN2016/089343, filed on Jul. 8, 2016.

(30) Foreign Application Priority Data

Jul. 23, 2015 (CN) .......................... 2015 1 0437275
Jul. 23, 2015 (CN) .......................... 2015 1 0437529

(51) Int. Cl.
| | | |
|---|---|---|
| C07F 7/08 | (2006.01) |
| C07C 67/11 | (2006.01) |
| C07C 45/51 | (2006.01) |
| C07C 45/64 | (2006.01) |
| C07F 7/18 | (2006.01) |
| G01N 30/02 | (2006.01) |
| G01N 30/88 | (2006.01) |

(52) U.S. Cl.
CPC .......... *C07F 7/0803* (2013.01); *C07C 45/516* (2013.01); *C07C 45/64* (2013.01); *C07C 67/11* (2013.01); *C07F 7/081* (2013.01); *C07F 7/1804* (2013.01); *C07C 2601/14* (2017.05); *G01N 30/02* (2013.01); *G01N 2030/884* (2013.01)

(58) Field of Classification Search
None
See application file for complete search history.

(56) References Cited

U.S. PATENT DOCUMENTS 4,429,145 A    1/1984   Reetz et al.

FOREIGN PATENT DOCUMENTS

| | | |
|---|---|---|
| DE | 3139456 A1 | 4/1983 |
| EP | 0076413 A2 | 4/1983 |
| EP | 0076413 A3 | 5/1984 |
| EP | 0076413 B1 | 9/1985 |
| IL | 66919 | 9/1982 |
| JP | S5872594 A | 4/1983 |
| JP | H0251916 B2 | 11/1990 |

OTHER PUBLICATIONS

Renzetti et al., Bull. of the Chem Soc of Japan (2014), (Year: 2014).*
Cao, Angew. Chem. Int. Ed. 2010, 49, 4976-4980. (Year: 2010).*
Renzettti et al., Bull. Chem. Soc. Jpn. vol. 87, No. I. 59-68 (2014) (Year: 2014).*
STN Results from CAS Registry; RN 1566565-82-9; Entered Mar. 11, 2014 (Year: 2014).*
Renzetti et al., Bull. of the Chem Soc of Japan (2014), 87(1 ), 59-68. (Year: 2014).*
15876464—STN Results—CAS Registry (Year: 2014).*
International Search Report dated Sep. 29, 2016 in International Application PCT/CN2016/089343.
Renzetti, Andrea et al., Si—CN Bond Cleavage of Silyl Cyanides by an Iron Catalyst. A New Route of Silyl Cyanide Formation, Bull. Chem. Soc. Jpn.,vol. 87, No. 1, Oct. 19, 2013 (Oct. 19, 2013), ISSN: 1348-0634, pp. 59-68.
Liu Yunlin et al., Organocatalytic Asymmetric Strecker Reaction of Di-and Trifluoromethyl Ketoimines. Remarkable Fluorine Effect, Organic letters, vol. 13, No. 15, Jun. 30, 2011 (Jun. 30, 2011), ISSN: 1523-7060, pp. 3826-3829.

(Continued)

*Primary Examiner* — Clinton A Brooks
*Assistant Examiner* — Kofi Adzamli
(74) *Attorney, Agent, or Firm* — Pillsbury Winthrop Shaw Pittman LLP

(57) ABSTRACT

The present teachings relate to a functionalized silyl cyanide and synthetic methods thereof. As an example, the method may include adding a raw material silane and a cyanide source MCN in an organic solvent to produce the functionalized silyl cyanide in the absence of catalyst or in the presence of a metal salt catalyst. The functionalized silyl cyanide may be used in the reactions that classic TMSCN participates in, to synthesize important intermediates (e.g., cyanohydrin, amino alcohols and α-amino nitrile compounds), with improved reactivity and selectivity. The cyanosilyl ether resulted from the nucleophilic addition of functionalized silyl cyanide to aldehyde or ketone may undergo intramolecular reaction under appropriate conditions to transfer the functional groups on silicon onto the other parts of the product linked to silicon. Such a functional group transfer process may increase the synthesis efficiency and atom economy, as well as afford products unobtainable using traditional TMSCN.

2 Claims, No Drawings

(56) References Cited

OTHER PUBLICATIONS

Tsang W.C.Peter, et al., "Evaluation of Enantiomerically Pure Binaphthol-Based Molybdenum Catalysts for Asymmetric Olefin . . . Generation and Decomposition of Unsubstituted Molybdacyclobutane Complexes", Organometallics, vol. 20, Nov. 29, 2001 (Nov. 29, 2001) ISSN: 0276-7333, pp. 5658-5669.

Zeng Xing-Ping et al., "Activation of Chiral (Salen)AlCl Complex by Phosphorane for Highly Enantioselective Cyanosilylation of Ketones and Enones", Journal of the American Chemical Society, vol. 138, Dec. 11, 2015 (Dec. 11, 2015) ISSN: 0002-7863, pp. 416-442.

Jackson, W. Roy et al. "Stereoselective Syntheses of Ephedrine and Related 2-Aminoalcohols of High Optical Purity from Protected Cyanohydrins", Tetrahedron Letters, vol. 31, No. 10, Dec. 31, 1990 (Dec. 31, 1990), ISSN: 0040-4039, pp. 1447-1450.

Weronika Waclawczyk-Biedron et al. "Synthesis of the Aggregation Pheromone of the Colorado Potato Beetle from Its Degradation Product", Bioorganic & Medicinal Chemistry Letters, vol. 25, Jun. 30, 2015 (Jun. 30, 2015), ISSN: 0960-8940, pp. 3560-3563.

Emilia Kiuru et al. "2, 2-Disubstituted 4-Acylthio-3-oxobutyl Groups as Esterase-and Thermolabile Protecting Groups of Phosphodiesters", Journal of Organic Chemistry, vol. 78, No. 3, Dec. 28, 2012 (Dec. 28, 2012), ISSN: 0022-3263, pp. 950-959.

Paul R Oritiz de Montellano et al. "Carboxylic and Phosphate Esters of α-Fluoro Alcohols", Journal of the American Chemical Society, vol. 101,No. 8,Apr. 11, 1979 (Apr. 11, 1979) ISSN: 0002-7863, pp. 2222-2224.

\* cited by examiner

FUNCTIONALIZED CYANOSILANE AND SYNTHESIS METHOD AND USE THEREOF

CROSS REFERENCE TO RELATED APPLICATIONS

The present application is a Continuation-In-Part application based on PCT/CN2016/089343, filed on Jan. 26, 2017, which claims the benefit of CN 2015104375294 and CN 2015104372756, both of which were filed on Jul. 23, 2015, the disclosures of which are fully incorporated herein by reference in their entireties.

BACKGROUND

1. Technical Field

The invention relates to technical field of organic compound processing application, specifically, to a functionalized silyl cyanide, a synthesis method and use thereof.

2. Technical Background

Nucleophilic addition reaction of cyanide to carbonyl compounds, imine and electron-deficient olefin etc. could be used for the synthesis of cyanohydrin, aminonitrile and nitrile compounds, and in particularly, the corresponding chiral products are very important chiral building block, which can be widely used in the synthesis of value-added fine chemicals, such as natural products, drug molecules, bioactive molecules and chiral ligands, etc. In addition, cyanide could undergo ring-opening reaction with epoxy, and aziridine, or participate in substitution and coupling reaction to selectively introduce cyano group. Therefore, developing new cyanating reagents has been of great interest to the chemical synthesis. Trimethylsilyl cyanide (TMSCN) is one of the most commonly used cyanating reagent, for the following advantages: 1) it is more convenient and secure to use than HCN, and 2) the trimethylsilyl group can be used as a protecting group for cyanohydrin. Therefore, it is widely used in cyanation reactions, especially in catalytic enantioselective cyanation reactions. However, the use of TMSCN as the cyanating reagent has some deficiencies:

In most of TMSCN participated reactions, the trimethylsilyl is not part of the target products, which can only be discharged in the form of by-products, thus compromised the overall atomic utilization of the reactions. As shown in Scheme (1), whether in the addition reaction, ring-opening reaction or coupling reaction, the trimethylsilyl in TMSCN is eventually discharged in the form of by-products (TMSX or TMSOH).

Scheme (1)

addition reaction:

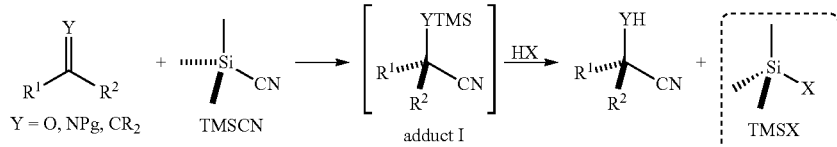

ring-opening reaction:

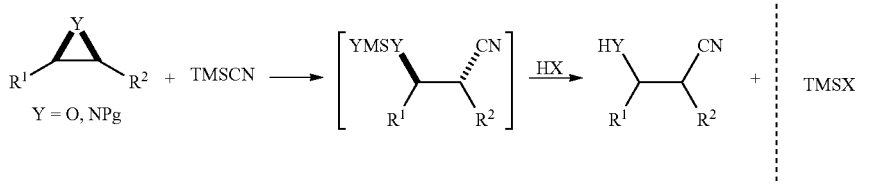

coupling reaction or substitution reaction:

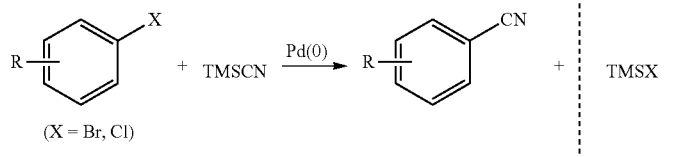

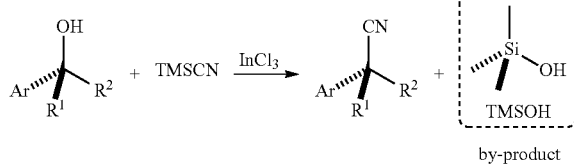

by-product

In some reactions, the reactivity of TMSCN is low. For example, in the ring-opening reaction of TMSCN to epoxide, Jacobsen et al found that, even using 10 mol % of chiral ytterbium catalyst, the reaction still took 7 days to achieve 83% yield (Org. Lett. 2000, 2, 1001).

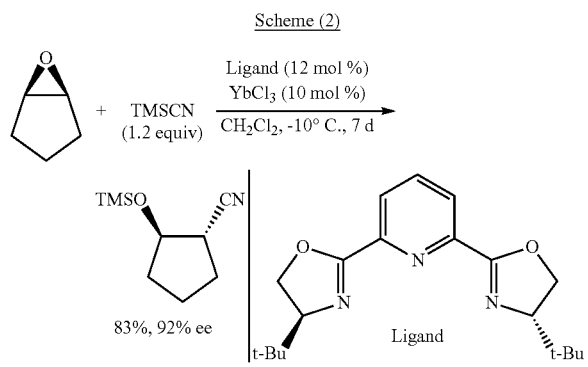

For some substrates, a high selectivity is difficult to achieve using TMSCN. For example, we found that in the nucleophilic addition reaction of TMSCN to alkenyl ketone, the target product could only be obtained with 80% ee, even at −30° C. (J. Am. Chem. Soc. 2016, 138, 416); as shown in Scheme (3).

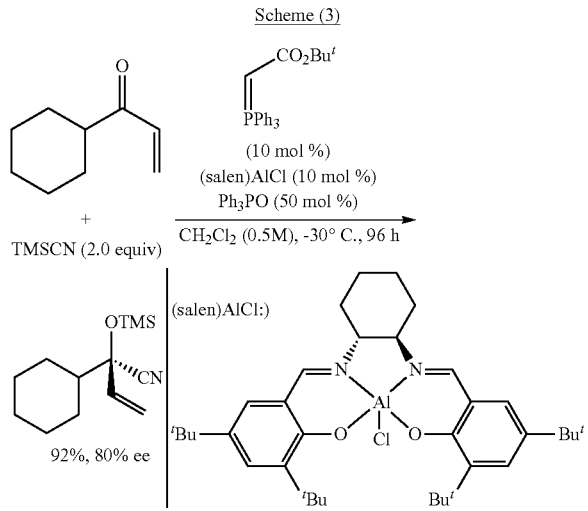

Therefore, there is a need to overcome the deficiencies of using TMSCN as a cyanating reagent. The present teaching aims to address those issues.

SUMMARY

The teachings disclosed herein relate provides a synthetic method for a series of novel functionalized silyl cyanide 1 with high yield by using commercially available silane compound 2 as the raw material, and commercially available MCN (including HCN or inorganic cyanides) as the cyanide source, cheap and readily available inorganic metal salt $NX^1_a$ as Lewis acid catalyst in common organic solvents. The novel functionalized silyl cyanide 1 synthesized in the invention can not only be used as highly efficient cyanating reagent to realize the nucleophilic addition reactions, ring-opening reactions, substitution reactions or coupling reactions which TMSCN participates in, but also can transfer the functional groups on the silyl group into the final product by tandem nucleophilic addition reaction/functional group transfer reaction, thus improving the overall atom utilization of the reaction. According to the functional groups on the silyl, the functionalized silyl cyanide 1 can also be used to design a series of tandem reaction, such as tandem nucleophilic addition reaction/radical addition reaction, tandem cyanosilylation reaction/ring-closing olefin metathesis reaction etc. to construct a series of silicon-containing heterocyclic compounds with new structure. In addition, the invention also provides a use of the functionalized silyl cyanide 1 in the total synthesis of the Colorado potato beetle aggregation pheromone (S)-1,3-dihydroxy-3,7-dimethyloct-6-en-2-one[(S)—CPB], as well as an intermediate compound in the synthesis.

The synthetic method for preparing the functionalized silyl cyanide 1 in the invention is as shown in Scheme (I), comprising the steps of: reacting a raw material silane compound 2 and HCN or inorganic cyanide via substitution reaction in the presence of a metal salt $NX^1_a$ (also known as Lewis acid catalyst $NX^1_a$) as the catalyst, in an organic solvent, thereby producing the novel functionalized silyl cyanide 1;

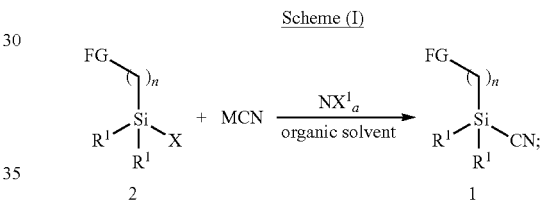

Wherein,
FG is selected from F, Cl, Br, I, $CHF_2$, $CHCl_2$, $-CH_2CH=CR_2$, $-CH=CR_2$, and $-C\equiv CR$; wherein, $-CH_2CH=CR_2$, $-CH=CR_2$ and $-C\equiv CR$ are functional groups having unsaturated carbon-carbon bond; wherein, R is H, Me;
$R^1$ is Me, Et;
X is selected from Cl, Br, I and OTf;
n=1-5.
Preferably, FG is selected from Cl, Br, $-CH_2CH=CH_2$, $-CH=CH_2$, and $-C\equiv CR$; wherein R is H, Me;
$R^1$ is Me;
X is Cl, Br;
n=1-3.
MCN is HCN or inorganic cyanides, wherein, M=H, Li, Na, K;
preferably, MCN is selected from HCN, NaCN and KCN.
The Lewis acid $NX^1_a$ represents inorganic salt, wherein, N=Li, Na, K, Mg, Zn, $X^1$=Br, I, OTf, a=1-3. Preferably, $NX^1_a$ is KI, $ZnI_2$.
Wherein, the reaction is conducted at a temperature of −20-200° C. under a nitrogen atmosphere; preferably, the reaction is conducted at a temperature of −20-120° C. under a nitrogen atmosphere.
Wherein, the silane compound 2 is commercially available raw material; MCN is a reagent used as the cyanide source.
The metal salt catalyst $NX^1_a$ is used for catalyzing the substitution reaction between the raw material 2 and MCN.

The product 1 is the corresponding novel cyanosilylation reagent, i.e. the functionalized silyl cyanide1.

Wherein, the molar ratio of silane compound 2, MCN and catalyst $NX^1_a$ is 100-300: 150-300: 3-9; preferably, is 100-200: 150-200: 3-9; more preferably, is 150: 200: 6.

The organic solvent is one or more of N,N-dimethylformamide (DMF), N,N-dimethylacetamide, dimethyl sulfoxide (DMA), tetrahydrofuran (THF), acetonitrile ($CH_3CN$), dichloromethane and toluene; preferably, is DMF, $CH_3CN$.

The novel cyanosilylation reagent 1 is the target product, and the silane compound 2 is commercially available raw material. Wherein, FG may be halogen atom such as F, Cl, Br, I; halogenated alkyl such as $CHF_2$, $CHCl_2$, etc.; functional groups having unsaturated carbon-carbon bonds such as —$CH_2CH=CR_2$, —$CH=CR_2$, —CCR (R=H or Me) et al.; $R^1$ is Me, Et.

The invention also provides a functionalized silyl cyanide represented by the following Formula (1), synthesized by the aforementioned synthesis method.

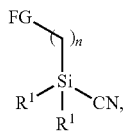

Formula (1)

Wherein,

FG is selected from F, Cl, Br, I, $CHF_2$, $CHCl_2$, —$CH_2CH=CR_2$, —$CH=CR_2$, and —CCR; wherein, —$CH_2CH=CR_2$, —$CH=CR_2$ and —C≡CR are functional groups having unsaturated carbon-carbon bond; wherein, R is H, Me;

$R^1$ is Me, Et;

n=1-5.

Preferably, FG is selected from Cl, Br, —$CH_2CH=CH_2$, —$CH=CH_2$, —CCR; Wherein, R is H, Me;

n=1-3.

The invention also provides a use of the functionalized silyl cyanide as shown in Formula (1) for nucleophilic addition reaction, comprising racemic nucleophilic addition reaction and asymmetric nucleophilic addition reaction; comprising the step of: reacting the functionalized silyl cyanide 1a and electrophilic reagent 3 under the catalysis of a catalyst I, to synthesize compound 4 by nucleophilic addition reaction; wherein, the compound 4 is in R and/or S configuration. The process of the reaction is as shown in Scheme (II):

Scheme (II)

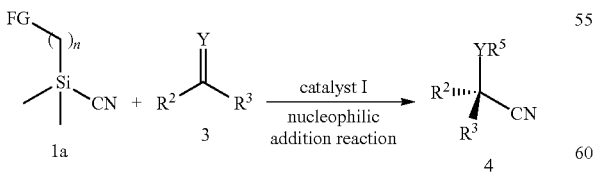

Wherein, the definitions of FG and n are the same as that in Scheme (I); CN is cyano group;

Y is selected from O, NBn, NCbz, NTs, NBoc, NPMP, NP(O)$Ph_2$, CHEWG (EWG=CN, $NO_2$, $CO_2R$, $CONR_2$, wherein, R=Me, Et, Ph, Bn);

$R^2$ is selected from C1-C20 alkyl, phenyl, C6-C20 substituted phenyl, naphthyl, C10-C20 substituted naphthyl, furanyl, C4-C10 substituted furanyl, thienyl, C4-C10 substituted thienyl, pyrryl, C4-C10 substituted pyrryl, pyridyl, and C5-C10 substituted pyridyl, et al.

Preferably, $R^2$ is selected from the groups consisting of the following Formula (a)~(l): wherein, the C6-C20 substituted phenyl is as shown in Formula (a), the C10-C20 substituted naphthyl is as shown in Formula (b) and (c), the C4-C10 substituted furanyl is as shown in Formula (d) and (e), the C4-C10 substituted thienyl is as shown in Formula (f) and (g), the C4-C10 substituted pyrryl is as shown in Formula (h) and (i), the C5-C10 substituted pyridyl is as shown in Formula (j) to (l);

(a)

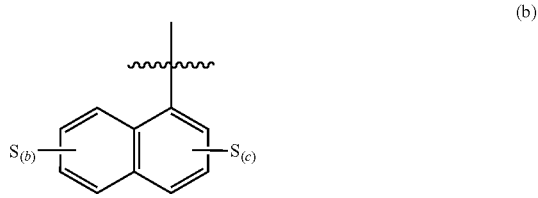
(b)

(c)

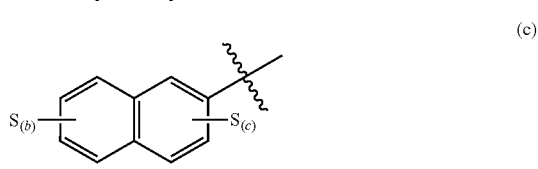
(d)

(e)

(f)

(g)

(h)

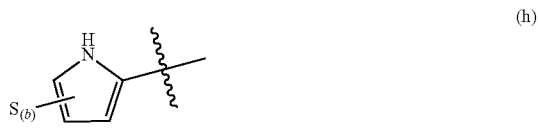

-continued

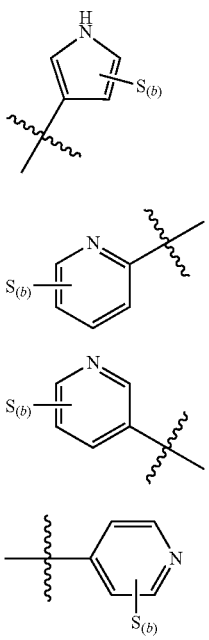

(i)

(j)

(k)

(l)

Wherein, for $S_{(b)}$ and $S_{(c)}$ of Formula (a) to (l), S is a substituent, and the substituent is selected from the group consisting of: same or different halogen; C1-C4 alkyl; C1-C4 alkoxyl; ester group (CO$_2$R, wherein, R=Me, Et, i-Pr, t-Bu, Ph, Bn); cyano group; nitro; acetal group and ketal group; b, c are the amount of the substituents, and b is an integer from 1 to 5 inclusive; c is an integer from 1 to 3 inclusive.

More preferably, $R^2$ is selected from C1-C20 alkyl, phenyl, C6-C20 substituted phenyl, naphthyl, C10-C20 substituted naphthyl, furanyl, C4-C10 substituted furanyl, thienyl, C4-C10 substituted thienyl, pyrryl, C4-C10 substituted pyrryl, pyridyl, C5-C10 substituted pyridyl, ester group (CO$_2$R, R=Me, Et), amide (CONR$_2$, R=Me, Et), et al.

Still more preferably, $R^2$ is selected from C1-C10 alkyl, phenyl, C6-C14 substituted phenyl, naphthyl, C10-C14 substituted naphthyl, furanyl, C4-C10 substituted furanyl, thienyl, C4-C10 substituted thienyl, pyrryl, C4-C10 substituted pyrryl, pyridyl, C5-C10 substituted pyridyl.

$R^3$ is selected from H; C1-C20 alkyl; ester group (CO$_2$R, wherein, R=Me, Et, i-Pr, t-Bu, Ph, Bn), amide (CONR$_2$, R=Me, Et, CF$_3$), et al.

Preferably, $R^3$ is selected from H; C1-C10 alkyl; ester group (CO$_2$R, wherein, R=Me, Et, t-Bu), amide (CONR$_2$, R=Me, Et), et al.

$R^5$ is H, or silyl on the functionalized silyl cyanide. When the substrates are not the same, the corresponding products are different.

The catalyst I is a nucleophilic addition reaction catalyst, used for catalyzing the nucleophilic addition reaction of the functionalized silyl cyanide 1a to the electrophilic reagent 3.

The nucleophilic addition reaction catalyzed by the catalyst I is conducted under a nitrogen atmosphere at a temperature of −50~150° C. while stirring until completion; preferably, the reaction temperature is −50~50° C.

The dosage of the catalyst I is 0.001-0.5 equivalent relative to the electrophilic reagent 3; preferably, is 0.001-0.1 equivalent.

The dosage of the functionalized silyl cyanide 1a is 1.0-5.0 equivalent relative to the electrophilic reagent 3; preferably, is 1.0-2.0 equivalent.

The racemic nucleophilic addition reaction and asymmetric nucleophilic addition reaction differ in that, the catalysts are not the same, with the other reaction conditions the same:

For the racemic nucleophilic addition reaction, the catalyst I′ comprises:

1) achiral inorganic Lewis base catalyst, comprising: inorganic metal carbonate comprising K$_2$CO$_3$, Li$_2$CO$_3$, Na$_2$CO$_3$, Cs$_2$CO$_3$; carboxylate comprising KOAc, LiOAc, NaOAc, CsOAc; and phosphate comprising K$_3$PO$_4$, Li$_3$PO$_4$, Na$_3$PO$_4$, et al.;

2) achiral organic Lewis base catalyst, such as: tertiary amine compounds comprising Et$_3$N, DABCO, i-Pr$_2$NEt; piperidine, pyridine derivatives comprising DMAP, N-methyl piperidine, oxynitride such as

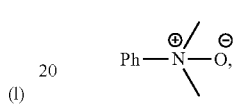

et al.;

3) achiral Lewis acid catalyst, comprising: metal salt comprising ZnI$_2$, KI, Zn(OTf)$_2$, TiCl$_4$.

For the asymmetric nucleophilic addition reaction, the catalyst I″ are common chiral catalysts suitable for silylcyanation reaction, comprising:

Chiral Lewis acid catalyst, chiral Lewis base catalyst, and chiral bifunctional catalyst having both Lewis acid functional group and Lewis base functional group co-existing in one molecule, and a variety of catalyst systems formed by chiral catalysts and achiral catalysts. Specifically, the catalyst I″ contains the catalysts as shown in the following Formula (IC1)~Formula (IC6):

Wherein, in Formula (IC1), $R^4$ is H, CH$_3$, OEt, Ot-Bu;

In Formula (IC2), $X^1$ is OTf, NTf$_2$;

In Formula (IC5), n is 1-5.

IC1

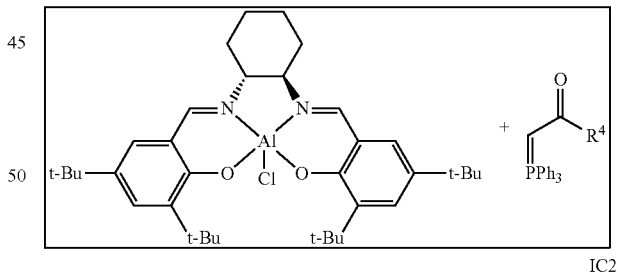

IC2

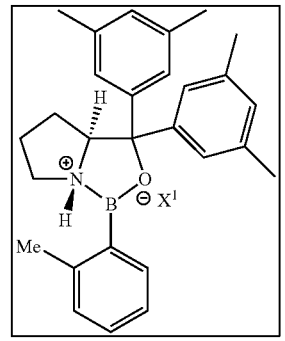

-continued

IC3
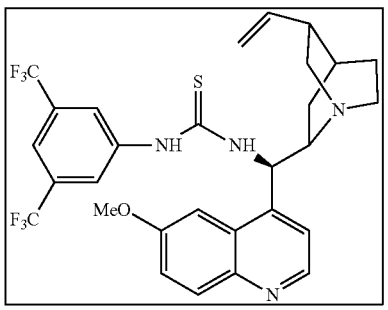

IC4
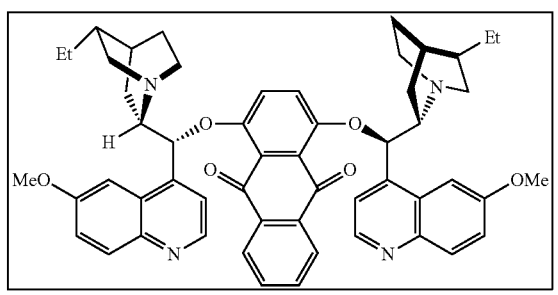

IC5
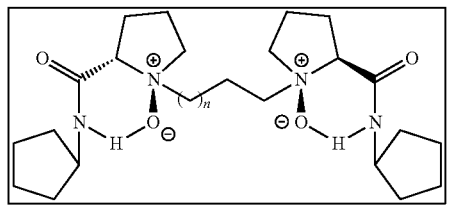

IC6
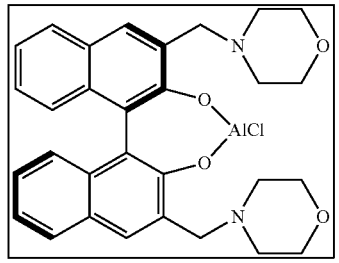

For the nucleophilic addition reaction, the general procedure comprises the following steps: the catalyst I, the raw material, an anhydrous solvent and the electrophilic reagent 3 are added into a dry Schlenk tube. The mixture is stirred and then added the functionalized silyl cyanide 1a. The progress of the reaction is monitored by TLC (thin-layer chromatography). After full consumption of the raw material, the reaction mixture is subject to column chromatography directly, and the yield could be determined.

The invention also provides the use of the functionalized silyl cyanide for synthesizing alcohols compounds bearing substituted ketone moiety, comprising racemic alcohols compounds and chiral alcohols compounds, via tandem nucleophilic addition reaction/functional group transfer reaction; comprising the step of: contacting functionalized silyl cyanide 1aa with a carbonyl compound 3a via nucleophilic addition reaction to provide an intermediate 4a which undergoes an intramolecular nucleophilic addition reaction promoted by base I and a hydrolysis reaction promoted by acid I; thereby producing an alcohols compounds 5 bearing substituted ketone moiety; the alcohols compounds 5 is in R and/or S configuration; the reaction process is as shown in Scheme (III):

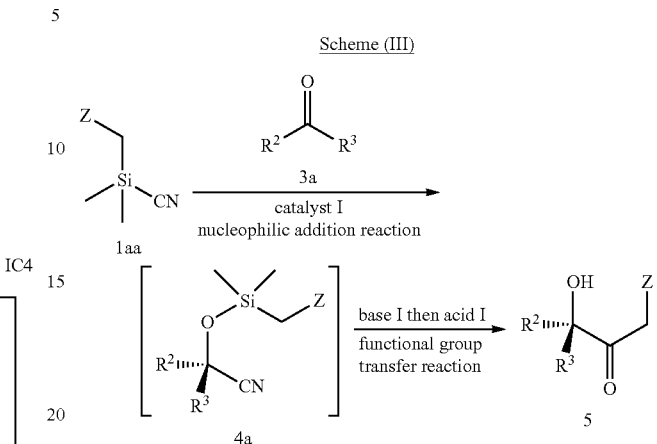

Wherein, the definition of $R^2$ and $R^3$ are the same as that in Scheme (II); CN is cyano group.

The catalyst I is used for catalyzing the nucleophilic addition reaction between the compound of Formula (1aa) and the compound of Formula (3a).

For the synthesis of racemic alcohols compounds, the catalyst I' used in the nucleophilic addition reaction is the same as the catalyst I' used in the racemic nucleophilic addition reaction as shown in Scheme (II); and the dosage of the catalyst I' can refer to that for Scheme (II).

For the synthesis of chiral alcohols compounds, the catalyst I" used in the nucleophilic addition reaction is the same as the catalyst I" used in the asymmetrical nucleophilic addition reaction as shown in Scheme (II); the dosage of the catalyst I" can refer to that for Scheme (II).

The reaction conditions of the nucleophilic addition reaction in the tandem nucleophilic addition reaction/functional group transfer reaction is the same as that for Scheme (II). The dosage of the corresponding compounds can refer to that for Scheme (II).

Z is Cl, Br. The base I is a strong base for removing hydrogen adjacent to FG, which is selected from LDA, NaHMDS, KHMDS; preferably, is LDA. The dosage of the base I is 1.0-3.0 equivalent relative to the intermediate compound 4a; preferably, is 1.0-2.0 equivalent.

The intramolecular nucleophilic attack reaction promoted by the base I is conducted under a temperature of −80-50° C., while stirring for completion.

The acid I is an acidic catalyst used for hydrolyzing C—Si and C═N bond, which is selected from hydrochloric acid, sulfuric acid, acetic acid; preferably, is hydrochloric acid. The dosage of the acid I is 10-50 equivalent relative to the intermediate compounds 4a; preferably, is 10-20 equivalent.

For tandem nucleophilic addition reaction/functional group transfer reaction, the general procedure is: the catalyst I, the raw material of 3a and a corresponding solvent were added into a dry Schlenk tube (25 mL). The mixture was added with 1aa after being stirred for 0.5 h. The progress of the reaction was monitored by TLC analysis. After the consumption of the raw material 3a is complete, the crude product 4a was obtained by filtering the reaction mixture through a 5 cm silica gel column, eluting with $Et_2O$, and removing solvent under reduced pressure. The crude product 4a was transferred to a dry Schlenk tube (25 mL) and dissolved with anhydrous THF. The resulting solution was added with a base I dropwise slowly. The progress of the reaction was monitored by TLC analysis. After the consumption of 4a was complete, the reaction was quenched by acid I. The resulting mixture was extracted three times by EtOAc. Product 5 as shown in Scheme (III) was obtained by combing the organic phase, and rotary evaporating to remove the solvent followed by column chromatography directly.

In one exemplary example, the invention also provides a use of the functionalized silyl cyanide for total synthesis of Colorado potato beetle aggregation pheromone (S)-1,3-dihydroxy-3,7-dimethyloct-6-en-2-one[(S)—CPB], comprising the following steps: contacting the functionalized silyl cyanide 1aa and carbonyl compound 6 in the presence of the catalyst I via nucleophilic addition reaction, thereby producing an intermediate 7;

Performing an intramolecular nucleophilic attack of the intermediate 7 under the action of LDA followed by a hydrolyzation in the presence of hydrochloric acid to afford a compound 8;

Reacting the compound 8 and KOAc by substitution reaction followed by a hydrolyzation in the presence of $K_2CO_3$, thereby producing the [(S)—CPB]; the reaction process is as shown in the following Scheme (IV),

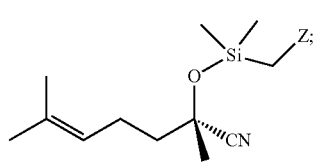

Formula (7)

Wherein: Z is Cl, Br.

The invention also provides a use of the functionalized silyl cyanide in tandem cyanosillalation reaction/ring-closing olefin metathesis reaction comprising racemic cyanosillalation reaction/ring-closing olefin metathesis reaction and asymmetric cyanosillalation reaction/ring-closing olefin metathesis reaction; comprising the following steps:

Reacting functionalized silyl cyanide 1ab and an alkenyl ketone 9 by cyanosillalation reaction in the presence of the catalyst I to produce an intermediate 10;

Performing an intramolecular ring-closing olefin metathesis reaction of the intermediate compound 10 in the presence of Grubbs I, thereby producing a silicon-containing heterocyclic compound 11;

Wherein, the silicon-containing heterocyclic compound 11 is in R and/or S configuration; and the process of the reaction is shown as in the following Scheme (V):

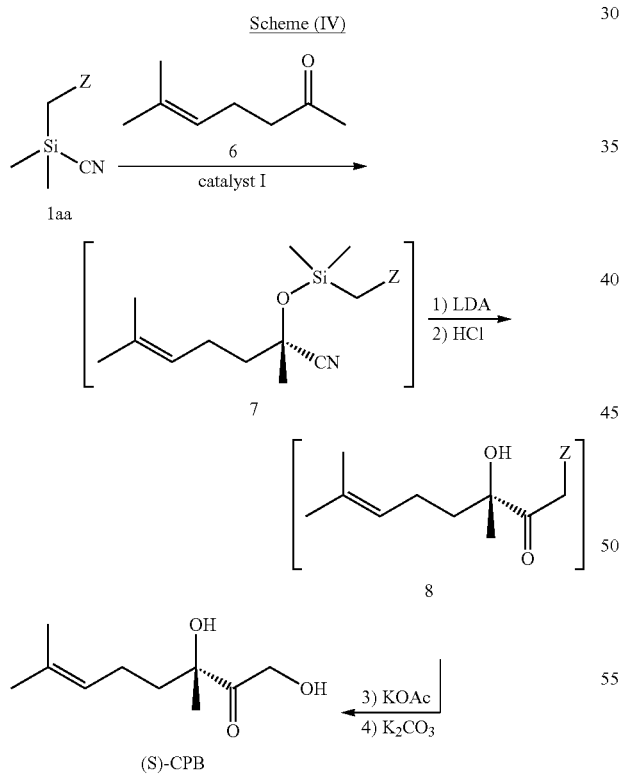

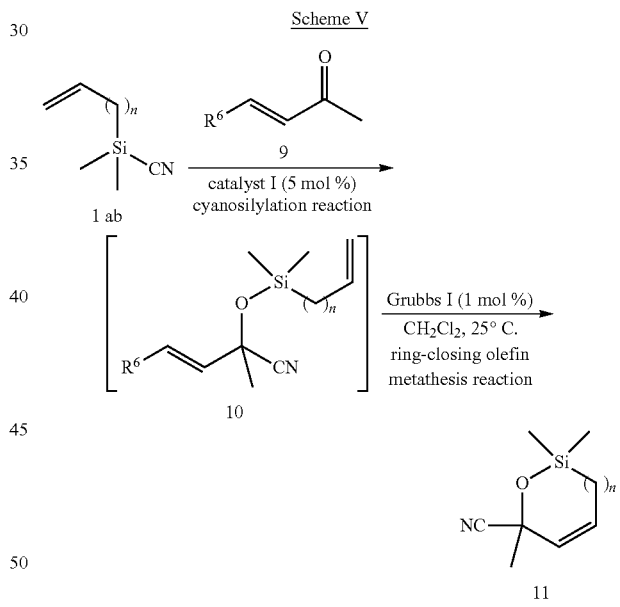

Wherein, n is 0, 1, or 2;

For racemic cyanosillalation reaction/ring-closing olefin metathesis reaction, the catalyst I used for the cyanosillalation reaction is $K_2CO_3$;

For asymmetric cyanosillalation reaction/ring-closing olefin metathesis reaction, the catalyst I used for the cyanosillalation reaction is IC1; and $R^6$ is H, Me, Et, Ph.

The invention also provides a use of the functionalized silyl cyanide for epoxy ring-opening reaction/functional group transfer reaction, comprising the following steps:

Reacting the functionalized silyl cyanide 1aa and an epoxy compound 12 in the presence of a catalyst I by epoxy ring-opening reaction to produce an intermediate 13;

Wherein, Z is Cl, Br;

The dosage of LDA is 1.0-3.0 equivalent relative to the intermediate compounds 7.

The invention also provides a new structural compound, i.e. an intermediate compound in the synthesis of (S)—CPB, which is represented by Formula (7), Performing an intramolecular nucleophilic attack of the intermediates compound 13 under the promotion of LDA followed by a hydrolyzation under the hydrolysis of hydrochloric acid to afford an alcohol compound 14;

Wherein, the alcohol compound 14 is in R and/or S configuration; and the epoxy ring-opening reaction/functional group transfer reaction comprises racemic epoxy ring-opening addition reaction/functional group transfer reaction and asymmetric epoxy ring-opening reaction/functional group transfer reaction; and the process of the reaction is as shown in the following Scheme (VI):

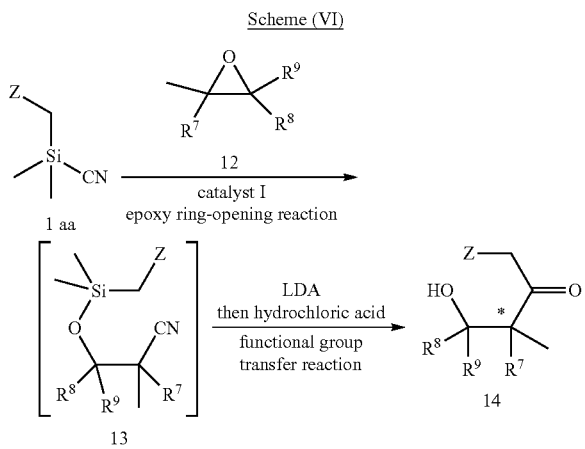

Wherein, the definitions of Z and the catalyst I are the same as that in Scheme (III); CN is cyano group;

$R^7$ is Me, Ph, Bn, $BnCH_2$;

$R^8$ and $R^9$ are H, Me, Et, Allyl; and $R^8$ and $R^9$ can be the same or different.

The present invention has the advantages that all the reagents used in the invention are commercially available, the source of the raw materials is wide, the raw materials are cost-effective, each reagent is stable under normal temperature and pressure, the operation are convenient, the catalyst used in the invention is relatively stable to air and moisture, the reactions are suitable for large-scale production; therefore the functionalized silyl cyanide synthesized in the invention has broad application prospect. The functionalized silyl cyanide could be used in the reactions which classic TMSCN participates in, to synthesize important intermediates such as cyanohydrin, amino alcohols and α-amino nitrile compounds, with better reactivity and selectivity, etc. Especially the products resulted from the nucleophilic addition reaction of functionalized silyl cyanide to carbonyl compounds could undergo intramolecular reaction under appropriate conditions to transfer the functional groups on silicon onto the other parts which is linked to silicon of the product. Such a functional group transfer process could not only increase the synthesis efficiency and atom economy, but also afford products which cannot be obtained by traditional TMSCN reagent. The asymmetric synthesis of (S)-1,3-dihydroxy-3,7-dimethyloct-6-en-2-one [(S)—CPB], was realized from commercially available 6-methylhept-5-en-2-one (CAS: 110-93-0), and the functionalized silyl cyanide synthesized in the invention. The compound (S)—CPB synthesized in the present invention is a kind of aggregation pheromones secreted by male Colorado potato beetle, which is a potential effective hormone-like pesticide for both sexes of Colorado potato beetle.

Additional novel features will be set forth in part in the description which follows, and in part will become apparent to those skilled in the art upon examination of the following or may be learned by production or operation of the examples. The novel features of the present teachings may be realized and attained by practice or use of various aspects of the methodologies, instrumentalities and combinations set forth in the detailed examples discussed below.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The present disclosure generally relates to systems, methods, medium, and other implementations directed a series of novel functionalized silyl cyanide 1 are designed and synthesized in the present invention. In principle, the functionalized silyl cyanide 1 could participate in all reactions which could be realized by TMSCN. In principle, the functionalized silyl cyanide 1 could participate in all reactions which could be realized by TMSCN. In addition, the functionalized silyl cyanide 1 also has the following three advantages:

First, the introduction of the functional group (FG) has certain influence on the steric and electrical property of the silicon atom, and makes the functionalized silyl cyanide 1 more reactive or selective than TMSCN.

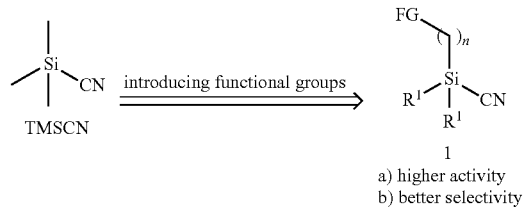

a) higher activity
b) better selectivity

In nucleophilic addition reaction of the functionalized silyl cyanide 1 to carbonyl compounds, the adduct could occur intramolecular reaction under appropriate conditions, to transfer the functional groups on the silyl into the final product. It not only enables the utilization of the functional groups on the silyl, thus improves the overall atomic utilization of the reaction, but also realizes the conversions which are difficult to be achieved in intermolecular fashion.

The invention now being generally described, it will be more readily understood by reference to the following examples which are included merely for purpose of illustration of certain aspects and examples of the present invention, and are not intended to limit the invention.

1) Conversion from Compound 2a to Compound 1aaa (Table 1)

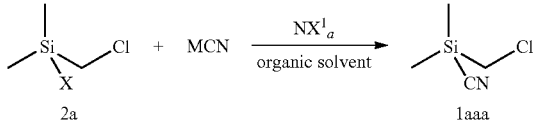

General procedure 1: a newly distilled 2a (100-300 mmol), MCN (150-300 mmol), a catalyst $NX^1_a$ (3-9 mmol) and an organic solvent (100 mL) were added into a dry three-necked flask (250 mL). The mixture was stirred at a temperature shown in Table 1. The progress of the reaction was monitored by GC analysis. After the consumption of the raw material 2a was complete, 1aaa as shown in Scheme (Ia) was obtained through reduced pressure distillation.

The specific experimental operations of the examples 1-17 are referred to general procedure 1. The specific reaction conditions and yield of each example are shown in Table 1. Wherein, 2a in Scheme (Ia) represents 2aa-2ad in Table 1 respectively.

The specific experimental operations of the examples 18-37 are referred to general procedure 2. The specific reaction conditions and yield of each example are shown in

TABLE 1

Specific reaction conditions and yields of the examples 1-17.

| Example | 2a (X) (mmol)/MCN (mmol)/NX$^1_a$ (mmol) | Solvent | Temperature (° C.) | Time (h) | Yield (%) |
|---|---|---|---|---|---|
| 1 | 2aa Cl (150)/HCN (200)/KI (6) | THF | 0 | 48 | 66 |
| 2 | 2aa Cl (150)/LiCN (200)/KI (6) | toluene | 150 | 36 | 37 |
| 3 | 2aa Cl (150)/NaCN (200)/KI (6) | THF | 80 | 24 | 68 |
| 7 | 2aa Cl (150)/NaCN (200)/LiI (6) | DMA | 150 | 36 | 34 |
| 8 | 2aa Cl (100)/NaCN (150)/NaI (6) | THF | 100 | 36 | 66 |
| 9 | 2aa Cl (100)/NaCN (150)/MgI$_2$ (6) | THF | 80 | 36 | 37 |
| 10 | 2aa Cl (100)/NaCN (150)/ZnI$_2$ (6) | THF | 80 | 36 | 74 |
| 11 | 2aa Cl (300)/NaCN (300)/KI (6) | DMF | 120 | 72 | 67 |
| 12 | 2aa Cl (200)/NaCN (250)/KI (3) | DMF | 120 | 72 | 73 |
| 13 | 2aa Cl (200)/NaCN (150)/KI (9) | DMF | −20 | 30 | 40 |
| 14 | 2ab Br (100)/NaCN (150)/KI (6) | THF | 80 | 34 | 68 |
| 15 | 2ac I (100)/NaCN (150)/KI (6) | THF | 80 | 24 | 66 |
| 16 | 2ad OTf (100)NaCN (150)/KI (6) | THF | 80 | 72 | 35 |
| 17 | 2ad OTf (100)NaCN (150)KI (6) | CH$_3$CN | 25 | 48 | 65 |

The characterization of compound 1aaa is as follows:

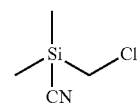

1aaa $^1$H NMR (400 MHz, CDCl$_3$): 2.96 (s, 2H), 0.48 (s, 6H);
$^{13}$C NMR (100 MHz, CDCl$_3$): δ 124.63, 26.94, −4.73;

2) Conversion from Compound 2 to Compound 1 (Table 2)

Scheme (Ib)

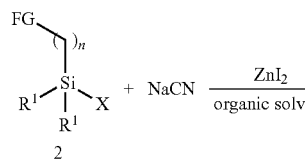

General procedure 2: a newly distilled halogenated silane 2 (150 mmol), NaCN (200 mmol), catalyst ZnI$_2$ (6 mmol) and an organic solvent (100 mL) were added into a dry 250 mL three-necked flask. The mixture was stirred at a temperature shown in Table 2. The progress of the reaction was monitored by GC analysis. After the full consumption of the raw material halogenated silane 2, compound 1 as shown in Scheme (Ib) was obtained by reduced pressure distillation.

Table 2. Wherein, 2 in Scheme (Ib) represents 2b-2m in Table 2, and 1 represents 1aab-1abd in Table 2 respectively.

TABLE 2

Specific reaction conditions and yields of the examples 18-37.

| Example | 2 | Solvent | Temperature (° C.) | Time (h) | Product/Yield (%) |
|---|---|---|---|---|---|
| 18 | ![2b] 2b | THF | 80 | 48 | 1aab/66 |
| 19 | 2b | DMA | 150 | 24 | 1aab/78 |
| 20 | 2b | CH$_3$CN | 100 | 24 | 1aab/77 |
| 21 | ![2c] 2c | THF | 80 | 36 | 1aba/67 |
| 22 | 2c | DMA | 150 | 36 | 1aba/34 |
| 23 | 2c | CH$_3$CN | 100 | 36 | 1aba/37 |
| 24 | ![2d] 2d | THF | 80 | 36 | 1abb/44 |
| 25 | 2d | DMA | 150 | 72 | 1abb/73 |
| 26 | 2d | CH$_3$CN | 100 | 72 | 1abb/56 |

TABLE 2-continued

Specific reaction conditions and yields of the examples 18-37.

| Example | 2 | Solvent | Temperature (° C.) | Time (h) | Product/Yield (%) |
|---|---|---|---|---|---|
| 27 | 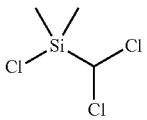 2e | THF | 80 | 34 | 1aca/68 |
| 28 | 2e | DMA | 150 | 72 | 1aca/35 |
| 29 | 2e | CH₃CN | 100 | 48 | 1aca/77 |
| 30 |  2f | CH₃CN | 100 | 48 | 1bba/75 |
| 31 | 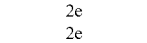 2g | CH₃CN | 80 | 48 | 1ada/42 |
| 32 | 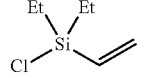 2h | CH₃CN | 80 | 24 | 1adb/71 |
| 33 | 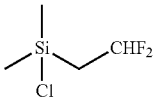 2i | CH₃CN | 80 | 24 | 1aea/74 |
| 34 | 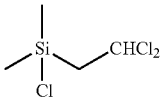 2j | CH₃CN | 80 | 24 | 1aeb/49 |
| 35 | 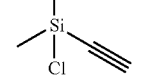 2k | CH₃CN | 80 | 24 | 1abc/67 |
| 36 | 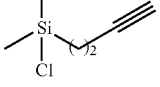 2l | CH₃CN | 80 | 24 | 1aec/46 |
| 37 | 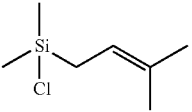 2m | CH₃CN | 80 | 24 | 1abd/58 |

The characterizations of 1aab-1abd are as follows:

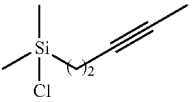

1aab $^1$H NMR (400 MHz, CDCl$_3$): 3.3 (s, 2H), 0.38 (s, 6H); $^{13}$C NMR (100 MHz, CDCl$_3$): δ 128.23, 27.89, −4.78;

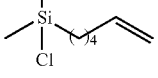

1aba $^1$H NMR (400 MHz, CDCl$_3$): 5.42 (d, 1H), 5.36 (s, 1H), 5.16 (d, 1H), 0.40 (s, 6H); $^{13}$C NMR (100 MHz, CDCl$_3$): δ 138.0, 124.9, 118.9, −4.05;

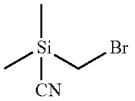

1abb $^1$H NMR (400 MHz, CDCl$_3$): 5.35 (dd, 1H), 5.24 (m, 2H), 2.08 (t, 2H), 0.43 (s, 6H); $^{13}$C NMR (100 MHz, CDCl$_3$): δ 135.0, 121.7, 119.8, 12.9, −4.09;

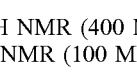

1aca $^1$H NMR (400 MHz, CDCl$_3$): 4.96 (s, 1H), 0.58 (s, 6H); $^{13}$C NMR (100 MHz, CDCl$_3$): δ 128.6, 56.7, −6.73.

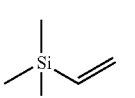

1bba $^1$H NMR (400 MHz, CDCl$_3$): 5.14 (dd, 1H), 5.05 (m, 2H), 0.78 (t, 6H), 0.43 (q, 4H); $^{13}$C NMR (100 MHz, CDCl$_3$): δ 128.0, 115.7, 110.1, 12.9, −3.78;

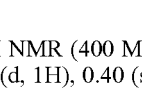

1ada $^1$H NMR (400 MHz, CDCl$_3$): 5.4 (t, 1H), 1.37 (m, 2H), 0.08 (d, 6H); $^{13}$C NMR (100 MHz, CDCl$_3$): δ 117.8, 115.5, 22.1, −2.6;

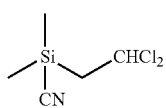
1adb

¹H NMR (400 MHz, CDCl₃): 5.3 (t, 1H), 1.36 (m, 2H), 0.08 (d, 6H); ¹³C NMR (100 MHz, CDCl₃): δ 116.8, 112.6, 25.1, −2.7;

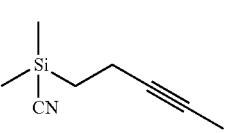
1aec

¹H NMR (400 MHz, CDCl₃): 2.22 (t, 2H), 2.03 (s, 3H), 1.22 (t, 2H), 0.11 (s, 6H); ¹³C NMR (100 MHz, CDCl₃): δ 122.0, 83.3, 78.5, 14.0, 11.9, 3.7, −2.9;

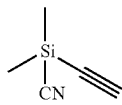
1aea

¹H NMR (400 MHz, CDCl₃): 2.81 (s, 1H), 0.13 (s, 6H); ¹³C NMR (100 MHz, CDCl₃): δ 117.3, 90.5, 89.5, 0.6;

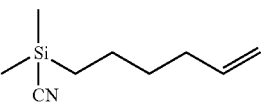
1abd

¹H NMR (400 MHz, CDCl₃): 5.82 (dd, 1H), 5.07 (d, 1H), 5.00 (d, 1H), 2.19 (m, 2H), 1.39 (m, 2H), 1.30 (m, 2H), 1.04 (t, 2H), 0.10 (s, 6H); ¹³C NMR (100 MHz, CDCl₃): δ 139.4, 119.3, 118.8, 33.8, 32.0, 23.3, 15.4, −2.3.

3) Nucleophilic Addition Reaction of Functionalized Silyl Cyanide 1aaa to Aldehydes or Ketones (Table 3).

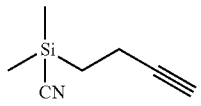
1aeb

¹H NMR (400 MHz, CDCl₃): 2.83 (s, 1H), 2.31 (t, 2H), 1.18 (t, 2H), 0.10 (s, 6H); ¹³C NMR (100 MHz, CDCl₃): δ 117.5, 86.2, 69.7, 13.9, 13.6, −2.8;

Scheme (IIa)

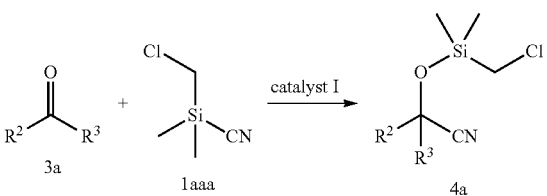

General procedure 3: a catalyst I, aldehyde or ketone 3a (1.0 mmol) and corresponding solvent (1 mL) were added into a dry Schlenk tube (25 mL). After being stirred at a corresponding temperature for 0.5 h, 1aaa (2.0 mmol) was added to the mixture. The reaction process was monitored by TLC analysis. After full consumption of raw material 3a, 4a as shown in Scheme (IIa) was obtained by conventional post-treatment followed by column chromatography, or by column chromatography directly.

The specific experimental operations of the examples 38-115 are referred to general procedure 3. The specific reaction conditions and yield of each example are shown in Table 3.

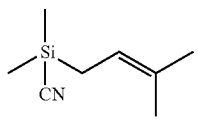
1abc

¹H NMR (400 MHz, CDCl₃): 5.22 (dd, 1H), 2.07 (d, 2H), 1.82 (m, 3H), 1.74 (d, 3H), 0.10 (s, 6H); ¹³C NMR (100 MHz, CDCl₃): δ 132.5, 120.3, 118.5, 28.0, 17.9, 11.4, −2.3;

TABLE 3

Specific reaction conditions and yields of the examples 38-115.

| Example | R² | R³ | Catalyst I (mol %) | Solvent | Temperature | Product/Yield (%)/Ee (%) |
|---|---|---|---|---|---|---|
| 38 | C₆H₅ | H | Li₂CO₃ (5) | CH₃CN | 25 | 4aa/76/— |
| 39 | C₆H₅ | Me | Na₂CO₃ (5) | DMF | 25 | 4ab/88/— |
| 40 | C₆H₅ | Et | K₂CO₃ (5) | DMSO | 25 | 4ac/85/— |
| 41 | C₆H₅ | i-Pr | K₂CO₃ (25) | CH₃CN | 50 | 4ad/90/— |
| 42 | C₆H₅ | allyl-CMe= | K₂CO₃ (25) | CH₃CN | 50 | 4ae/92/— |

TABLE 3-continued

Specific reaction conditions and yields of the examples 38-115.

| Example | R² | R³ | Catalyst I (mol %) | Solvent | Temperature | Product/ Yield (%)/ Ee (%) |
|---|---|---|---|---|---|---|
| 43 | C₆H₅ | CO₂Me | KOAc (25) | CH₃CN | 25 | 4af/95/— |
| 44 | C₆H₅ | CO₂Bn | KOAc (25) | CH₃CN | 25 | 4ag/79/— |
| 45 | C₆H₅ | CONMe₂ | CsOAc (25) | CH₃CN | 25 | 4ah/83/— |
| 46 | C₆H₅ | CONEt₂ | LiOAc (25) | THF | 50 | 4ai/85/— |
| 47 | C₆H₅ | Cy | KOAc (50) | CH₃CN | 50 | 4aj/88/— |
| 48 | C₆H₅ | [1-methylallyl group] | KOAc (25) | DMF | 25 | 4ak/79/— |
| 49 | C₆H₅ | [1-methyl-2-butenyl group] | K₂CO₃ (15) | THF | 25 | 4al/77/— |
| 50 | C₆H₅ | [1,3-dimethyl-2-butenyl group] | K₂CO₃ (15) | CH₃CN | 80 | 4am/75/— |
| 51 | C₆H₅ | [1-methylpropargyl group] | K₂CO₃ (15) | DMF | 25 | 4an/69/— |
| 52 | 4-Cl—C₆H₄ | Me | Et₃N (5) | THF | 40 | 4ao/88/— |
| 53 | 3-Cl—C₆H₄ | Me | Ph—N⁺(Me)—O⁻ (25) | toluene | 50 | 4ap/85/— |
| 54 | 4-F—C₆H₄ | Me | Et₃N (25) | CH₂Cl₂ | 25 | 4ar/81/— |
| 55 | 4-Br—C₆H₄ | Me | (i-Pr)₂NEt (25) | CH₃CN | 25 | 4as/81/— |
| 56 | 3,4-Cl₂—C₆H₃ | Et | Et₃N (25) | CH₂Cl₂ | 25 | 4at/60/— |
| 57 | 2,4,6-Me₂—C₆H₂ | H | DMAP (30) | CH₃CN | 50 | 4au/90/— |
| 58 | 4-NO₂—C₆H₄ | Me | Ph—N⁺(Me)—O⁻ (5) | DMF | 25 | 4av/85/— |
| 59 | 4-Et—C₆H₄ | Me | K₂CO₃ (25) | THF | 0 | 4aw/85/— |
| 60 | 4-Me—C₆H₄ | H | K₂CO₃ (15) | THF | 0 | 4ax/82/— |
| 61 | Cy | H | Zn(OTf)₂ (0.1) | CH₃CN | 25 | 4ay/85/— |
| 62 | Cy | Me | K₂CO₃ (1) | DMF | 50 | 4az/97/— |
| 63 | 2-naphthyl | Me | K₂CO₃ (5) | THF | 50 | 4aaa/80/— |

TABLE 3-continued

Specific reaction conditions and yields of the examples 38-115.

| Example | R² | R³ | Catalyst I (mol %) | Solvent | Temperature | Product/Yield (%)/Ee (%) |
|---|---|---|---|---|---|---|
| 64 | 1-naphthyl | H | K₂CO₃ (2.5) | toluene | 10 | 4aab/92/— |
| 65 | 7-methyl-2-naphthyl | H | K₃PO₄ (2.5) | CH₂Cl₂ | 10 | 4aac/90/— |
| 66 | 3-methyl-2-naphthyl | H | Na₂PO₄ (2.5) | DMF | 25 | 4aad/75/— |
| 67 | 7-methyl-1-naphthyl | Me | K₂CO₃ (10) | THF | 25 | 4aae/95/— |
| 68 | 2,3-dihydrobenzo[1,4]dioxin-6-yl | Me | K₂CO₃ (10) | CH₃CN | 25 | 4aaf/89/— |
| 69 | benzo[1,3]dioxol-5-yl | Me | KI (10) | DMF | 25 | 4aag/91/— |
| 70 | Bn | Me | K₂CO₃ (5) | THF | 50 | 4aah/93/— |
| 71 | 5-(methoxycarbonyl)furan-2-yl | H | K₂CO₃ (2.5) | CH₃CN | 25 | 4aai/88/— |
| 72 | furan-2-yl | Me | TiCl₄ (0.5) | toluene | 0 | 4aaj/75/— |
| 73 | 5-methylfuran-2-yl | Me | ZnI₂ (0.5) | CH₃CN | 25 | 4aak/84/— |
| 74 | 5-methylthiophen-2-yl | Me | TiCl₄ (0.5) | toluene | 0 | 4aal/79/— |

TABLE 3-continued

Specific reaction conditions and yields of the examples 38-115.

| Example | R² | R³ | Catalyst I (mol %) | Solvent | Temperature | Product/Yield (%)/Ee (%) |
|---|---|---|---|---|---|---|
| 75 | 2-methyl-1H-pyrrol-5-yl | Me | ZnI₂ (0.5) | CH₃CN | 25 | 4aam/85/— |
| 76 | 6-methylpyridin-2-yl | Me | KI (2.5) | CH₃CN | 50 | 4aan/85/— |
| 77 | BnCH₂ | Me | K₂CO₃ (2) | CH₃CN | 50 | 4aao/95/— |
| 78 | 5-methylpyridin-2-yl | Me | K₂CO₃ (2.5) | THF | 25 | 4aap/85/— |
| 79 | 4-methylpyridin-2-yl | Me | K₂CO₃ (2.5) | THF | 25 | 4aaq/90/— |
| 80 | t-Bu | H | Zn(OTf)₂ (1) | toluene | 25 | 4aar/94/— |
| 81 | Et | H | Zn(OTf)₂ (1) | toluene | 25 | 4aas/80/— |
| 82 | i-Pr | H | Zn(OTf)₂ (1) | toluene | 25 | 4aat/87/— |
| 83 | C₆H₅ | Me | IC1 (10) (R⁴ = Me) | CH₂Cl₂ | 0 | 4ab/88/85 |
| 84 | C₆H₅ | Et | IC1 (10) (R⁴ = OEt) | Et₂O | 0 | 4ac/85/83 |
| 85 | C₆H₅ | i-Pr | IC1 (10) (R = Ot—Bu) | Et₂O | 0 | 4ad/90/75 |
| 86 | C₆H₅ | but-3-en-1-yl | IC1 (20) (R = OEt) | Et₂O | 0 | 4ae/92/60 |
| 87 | C₆H₅ | CO₂Me | IC4 (10) | toluene | 25 | 4af/95/77 |
| 88 | C₆H₅ | CONMe₂ | IC4 (20) | toluene | 25 | 4ah/83/80 |
| 89 | C₆H₅ | Cy | IC6 (10) | CH₂Cl₂ | 20 | 4aj/88/90 |
| 90 | C₆H₅ | allyl | IC1 (10) (R⁴ = OEt) | CH₂Cl₂ | 25 | 4ak/79/95 |
| 91 | C₆H₅ | but-2-en-1-yl | IC1 (10) (R⁴ = OEt) | CH₂Cl₂ | 25 | 4al/77/86 |
| 92 | C₆H₅ | but-2-yn-1-yl | IC1 (10) (R⁴ = OEt) | CH₂Cl₂ | 25 | 4an/69/80 |
| 93 | 4-Cl—C₆H₄ | Me | IC2 (10) (X¹ = NTf₂) | toluene | -40 | 4ao/88/94 |
| 94 | 3-Cl—C₆H₄ | Me | IC2 (10) (X¹ = NTf₂) | toluene | -40 | 4ap/85/92 |
| 95 | 2-Cl—C₆H₄ | H | IC2 (10) (X¹ = OTf) | THF | -50 | 4aq/87/84 |
| 96 | 4-F—C6H4 | Me | IC2 (10) (X¹ = NTf₂) | CH₂Cl₂ | -40 | 4ar/81/90 |
| 97 | 4-Br—C₆H₄ | Me | IC2 (10) (X¹ = NTf₂) | toluene | -40 | 4as/81/89 |
| 98 | 3,5-Cl₂—C₆H₃ | H | IC2 (10) (X¹ = OTf) | THF | -40 | 4at/95/90 |
| 99 | 4-NO₂—C₆H₄ | Me | IC1 (10) (R⁴ = OEt) | toluene | -25 | 4av/85/97 |
| 100 | 4-Me—C₆H₄ | H | IC2 (10) (X¹ = OTf) | CH₂Cl₂ | -25 | 4ax/82/88 |
| 101 | Cy | H | IC2 (0.1) (X¹ = OTf) | THF | 25 | 4ay/85/94 |
| 102 | Cy | Me | IC1 (10) (R⁴ = OEt) | Et₂O | -50 | 4az/97/95 |

TABLE 3-continued

Specific reaction conditions and yields of the examples 38-115.

| Example | R² | R³ | Catalyst I (mol %) | Solvent | Temperature | Product/Yield (%)/Ee (%) |
|---|---|---|---|---|---|---|
| 103 |  (2-naphthyl) | Me | IC3 (10) | toluene | 10 | 4aaa/80/93 |
| 104 | 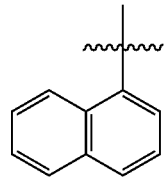 [SMILES: *c1cccc2ccccc12] (1-naphthyl) | H | IC2 (0.1) ($X^1$ = NTf$_2$) | toluene | −50 | 4aab/92/84 |
| 106 | 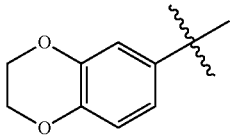 [SMILES: *c1ccc2c(c1)OCCO2] (2,3-dihydrobenzo[b][1,4]dioxin-6-yl) | Me | IC1 (10) ($R^4$ = OEt) | Et$_2$O | −30 | 4aaf/89/94 |
| 107 | 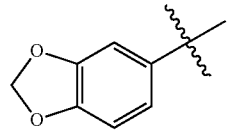 (benzo[d][1,3]dioxol-5-yl) | Me | IC1 (10) ($R^4$ = OEt) | Et$_2$O | −30 | 4aag/91/92 |
| 108 | Bn | Me | IC1 (10) ($R^4$ = OEt) | Et$_2$O | −30 | 4aah/93/97 |
| 109 | 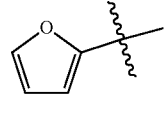 [SMILES: *c1ccco1] (furan-2-yl) | Me | IC1 (10) ($R^4$ = OEt) | Et$_2$O | −10 | 4aaj/75/82 |
| 110 | 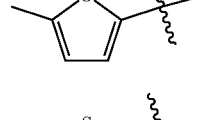 (5-methylfuran-2-yl) | Me | IC1 (10) ($R^4$ = OEt) | Et$_2$O | −30 | 4aak/84/84 |
| 111 | 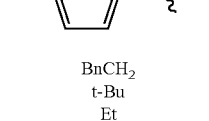 (5-methylthiophen-2-yl) | Me | IC1 (10) ($R^4$ = Ot—Bu) | toluene | −50 | 4aal/79/85 |
| 112 | BnCH$_2$ | Me | IC1 (10) ($R^4$ = OEt) | Et$_2$O | −30 | 4aao/95/96 |
| 113 | t-Bu | H | IC2 (0.1) ($X^1$ = OTf) | THF | 25 | 4aar/94/94 |
| 114 | Et | H | IC2 (0.1) ($X^1$ = OTf) | THF | 25 | 4aas/80/80 |
| 115 | i-Pr | H | IC2 (0.1) ($X^1$ = OTf) | THF | 25 | 4aat/87/89 |

The characterizations of 4aa-4aat are as follows:

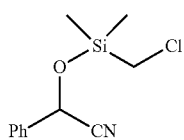

4aa $^1$H NMR (400 MHz, CDCl$_3$): δ 7.38-7.36 (m, 5H), 5.51 (s, 1H), 3.67 (dd, 2H), 0.21 (s, 6H); $^{13}$C NMR (100 MHz, CDCl$_3$): δ 133.7, 128.8, 128.0, 127.5, 118.2, 34.6, −0.4;

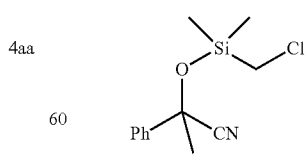

4ab $^1$H NMR (400 MHz, CDCl$_3$): δ 7.04-7.35 (m, 5H), 3.47 (dd, 2H), 1.87 (s, 3H), 0.22 (s, 6H); $^{13}$C NMR (100 MHz, CDCl$_3$): δ 136.7, 128.9, 128.0, 126.5, 119.2, 35.2, 30.9, −0.3;

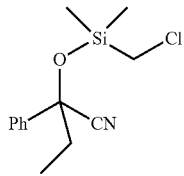
4ac

¹H NMR (400 MHz, CDCl₃): δ 7.40-7.36 (m, 5H), 3.46 (dd, 2H), 1.87 (q, 2H), 0.87 (t, 2H), 0.22 (s, 6H); ¹³C NMR (100 MHz, CDCl₃): δ 146.7, 128.8, 126.0, 125.5, 119.0, 35.2, 32.9, 4.2, -0.4;

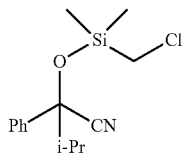
4ad

¹H NMR (400 MHz, CDCl₃): δ 7.49-7.32 (m, 5H), 2.72 (s, 2H), 2.66 (s, 1H), 0.90 (s, 6H), 0.21 (s, 6H); ¹³C NMR (100 MHz, CDCl₃): δ 140.84, 127.94, 127.68, 127.30, 121.50, 77.78, 41.09, 21.02, 16.79, -0.62;

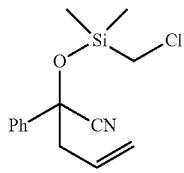
4ae

¹H NMR (400 MHz, CDCl₃): δ 7.47-7.32 (m, 5H), 5.82 (dd, 1H), 5.07-5.02 (m, 2H), 3.47 (dd, 2H), 2.66 (dd, 2H), 0.21 (s, 6H); ¹³C NMR (100 MHz, CDCl₃): δ 137.86, 132.96, 128.69, 127.71, 127.36, 121.57, 118.52, 85.81, 44.11, 21.02, -0.62;

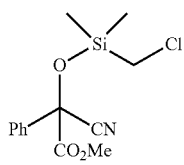
4af

¹H NMR (400 MHz, CDCl₃): δ 7.49-7.38 (m, 10H), 5.34 (s, 2H), 2.74 (dd, 2H), 0.21 (s, 6H); ¹³C NMR (100 MHz, CDCl₃): δ 162.33, 133.85, 130.96, 128.17, 127.75, 119.13, 71.2, 62.33, 52.61, 21.02, -0.62;

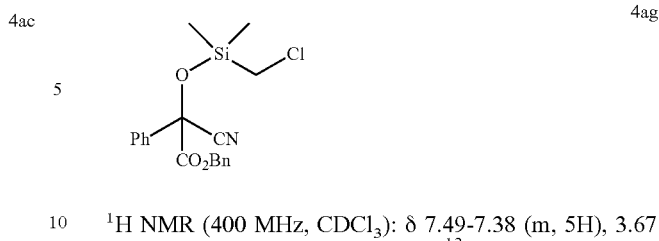
4ag

¹H NMR (400 MHz, CDCl₃): δ 7.49-7.38 (m, 5H), 3.67 (s, 3H), 2.72 (dd, 2H), 0.21 (s, 6H); ¹³C NMR (100 MHz, CDCl₃): δ 161.67, 137.56, 133.85, 130.96, 129.01, 128.19, 128.17, 128.16, 127.75, 119.13, 71.2, 67.31, 62.61, 21.02, -0.62;

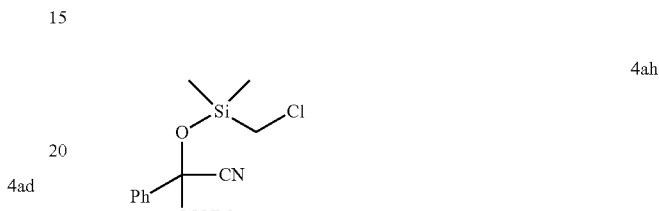
4ah

¹H NMR (400 MHz, CDCl₃): δ 7.42-7.34 (m, 5H), 3.44 (s, 6H), 2.59 (dd, 2H), 0.22 (s, 6H); ¹³C NMR (100 MHz, CDCl₃): δ 159.67, 131.22, 130.37, 129.41, 128.92, 111.80, 71.9, 64.00, 36.87, 21.02, -0.62;

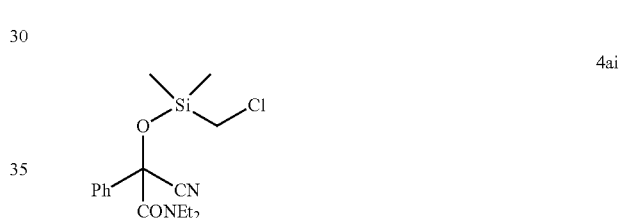
4ai

¹H NMR (400 MHz, CDCl₃): δ 7.40-7.34 (m, 5H), 3.44 (s, 6H), 2.52 (dd, 2H), 1.08 (t, 6H), 0.21 (s, 6H); ¹³C NMR (100 MHz, CDCl₃): δ 163.66, 131.22, 130.37, 129.41, 128.92, 111.80, 71.9, 62.78, 43.22, 21.02, 13.15, -0.62;

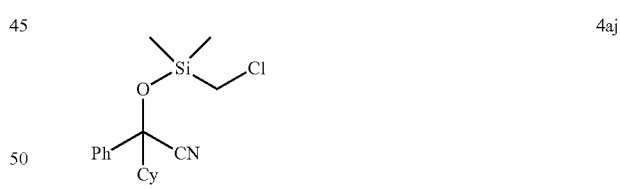
4aj

¹H NMR (400 MHz, CDCl₃): δ 7.40-7.36 (m, 5H), 2.52 (dd, 2H), 1.78-1.43 (m, 11H), 0.22 (s, 6H); ¹³C NMR (100 MHz, CDCl₃): δ 140.01, 127.85, 127.54, 127.26, 121.44, 71.96, 44.87, 71.3, 27.52, 25.89, 21.02, -0.62;

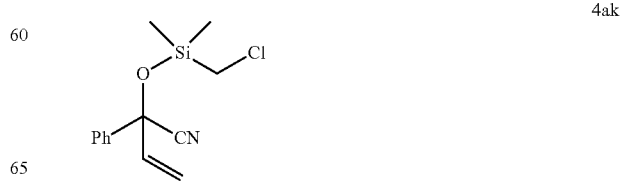
4ak

¹H NMR (400 MHz, CDCl₃): δ 7.38-7.30 (m, 5H), 6.20 (dd, 1H), 5.04-4.98 (m, 2H), 2.56 (dd, 2H), 0.21 (s, 6H); ¹³C NMR (100 MHz, CDCl₃): δ 137.94, 134.89, 129.12, 128.58, 127.86, 121.48, 121.27, 71.2, 21.02, −0.62;

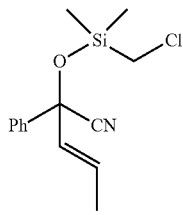

4al

¹H NMR (400 MHz, CDCl₃): δ 7.40-7.30 (m, 5H), 6.10 (dd, 1H), 5.55 (m, 1H), 2.56 (dd, 2H), 2.05 (d, 2H), 0.21 (s, 6H); ¹³C NMR (100 MHz, CDCl₃): δ 134.42, 133.10, 130.59, 129.62, 128.11, 127.75, 121.45, 71.2, 21.02, 19.10, −0.62;

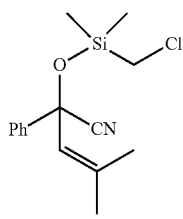

4am

¹H NMR (400 MHz, CDCl₃): δ 7.43-7.35 (m, 5H), 6.10 (s, 1H), 2.56 (dd, 2H), 2.05 (s, 3H), 1.98 (s, 3H), 0.21 (s, 6H); ¹³C NMR (100 MHz, CDCl₃): δ 146.94, 134.04, 130.20, 127.69, 124.59, 121.43, 71.2, 25.84, 21.02, 19.65, −0.62;

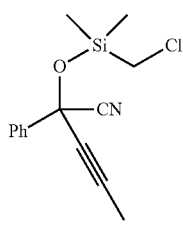

4an

¹H NMR (400 MHz, CDCl₃): δ 7.45-7.35 (m, 5H), 2.56 (dd, 2H), 1.88 (s, 3H), 0.21 (s, 6H); ¹³C NMR (100 MHz, CDCl₃): δ 132.03, 130.95, 128.11, 126.84, 104.69, 95.94, 78.15, 71.5, 21.02, 7.30, −0.62;

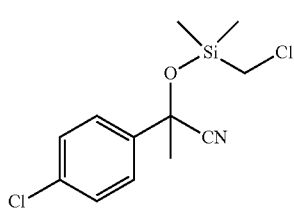

4ao

¹H NMR (400 MHz, CDCl₃): δ 7.50-7.38 (m, 5H), 2.83 (dd, 2H), 1.88 (s, 3H), 0.31 (s, 6H); ¹³C NMR (100 MHz, CDCl₃): δ 140.01, 135.12, 129.11, 126.12, 120.96, 71.55, 33.34, 29.57, −2.04, −2.12;

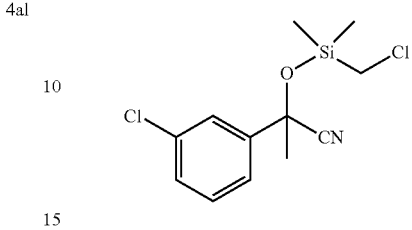

4ap

¹H NMR (400 MHz, CDCl₃): δ 7.54-7.35 (m, 5H), 2.85-2.80 (dd, 2H), 1.88 (s, 3H), 0.34 (s, 6H); ¹³C NMR (100 MHz, CDCl₃): δ 143.45, 135.01, 130.23, 129.31, 125.00, 122.86, 120.85, 71.48, 33.33, 29.54, −2.04, −2.12;

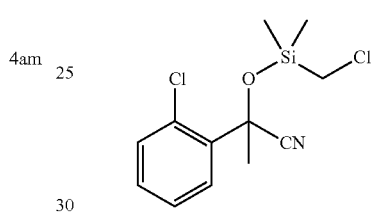

4aq

¹H NMR (400 MHz, CDCl₃): δ 7.58-7.36 (m, 5H), 2.87-2.79 (dd, 2H), 1.89 (s, 3H), 0.34 (s, 6H); ¹³C NMR (100 MHz, CDCl₃): δ 145.47, 136.01, 131.25, 129.71, 123.09, 121.86, 120.80, 71.48, 33.33, 29.54, −2.04, −2.12;

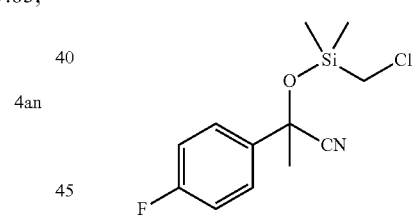

4ar

¹H NMR (400 MHz, CDCl₃): δ 7.52-7.38 (m, 5H), 2.81 (dd, 2H), 1.86 (s, 3H), 0.29 (s, 6H); ¹³C NMR (100 MHz, CDCl₃): δ 162.78, 136.32, 129.30, 123.36, 115.61, 72.39, 31.71, 21.02, −0.62;

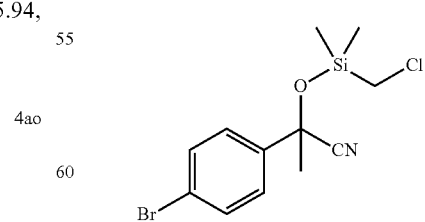

4as

¹H NMR (400 MHz, CDCl₃): δ 7.56-7.42 (m, 5H), 2.83 (dd, 2H), 1.86 (s, 3H), 0.32 (s, 6H); ¹³C NMR (100 MHz, CDCl₃): δ 140.54, 132.07, 126.40, 123.22, 120.89, 71.58, 33.30, 29.56, −2.04, −2.12;

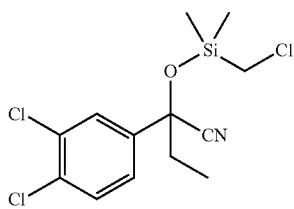

4at

¹H NMR (400 MHz, CDCl₃): δ 7.50 (s, 1H), 7.66-7.18 (m, 2H), 2.86-2.80 (dd, 2H), 1.87 (q, 2H), 0.90 (t, 3H), 0.30 (s, 6H); ¹³C NMR (100 MHz, CDCl₃): δ 135.27, 134.72, 131.86, 127.12 (d, J=8.0 Hz), 126.86, 121.95, 86.43, 38.52, 21.02, 7.77, −0.62.

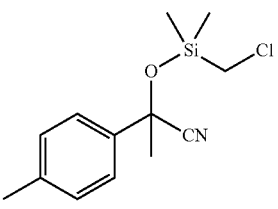

4ax

¹H NMR (400 MHz, CDCl₃): δ 7.20-7.00 (dd, 4H), 2.90 (dd, 1H), 2.30 (s, 3H), 1.82 (s, 3H), 0.30 (s, 3H); ¹³C NMR (100 MHz, CDCl₃): δ 138.02, 137.60, 128.16, 127.40, 123.36, 72.39, 31.71, 21.09 (d, J=15.7 Hz), −1.62.

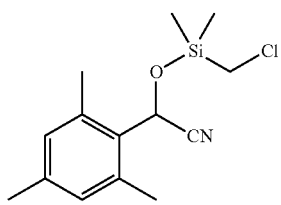

4au

¹H NMR (400 MHz, CDCl₃): δ 6.84 (s, 2H), 5.50 (s, 1H), 2.63 (dd, 2H), 2.38 (s, 6H), 2.30 (s, 3H), 0.21 (s, 6H); ¹³C NMR (100 MHz, CDCl₃): δ 140.28, 140.06, 129.81, 126.37, 118.63, 57.44, 28.43, 21.83, 20.50, −1.86.

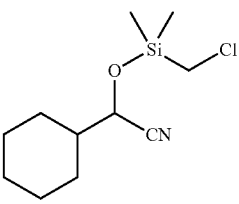

4ay

¹H NMR (400 MHz, CDCl₃): δ 4.20 (d, 1H), 2.97 (dd, 2H), 1.90 (m, 1H), 1.53-1.27 (m, 10H), 0.22 (s, 6H); ¹³C NMR (100 MHz, CDCl₃): δ 118.88, 65.71, 39.88, 28.93, 28.43, 25.92, 25.57, −1.86;

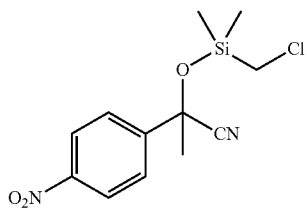

4av

¹H NMR (400 MHz, CDCl₃): δ 8.30-7.75 (m, 4H), 2.90 (dd, 1H), 1.92 (s, 3H), 0.38 (s, 3H), 0.36 (s, 3H); ¹³C NMR (100 MHz, CDCl₃): δ 148.30, 148.16, 125.78, 124.19, 120.38, 71.32, 33.32, 29.42, −1.95, −2.07;

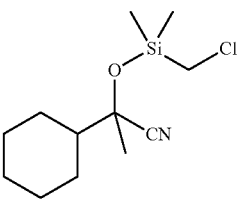

4az

¹H NMR (400 MHz, CDCl₃): δ 2.87 (dd, 2H), 1.96 (d, 1H), 1.84-1.81 (m, 3H), 1.69 (d, J=10.8 Hz, 1H), 1.56 (s, 3H), 1.52-1.48 (m, 1H), 1.26-1.07 (m, 5H), 0.38 (s, 6H); ¹³C NMR (100 MHz, CDCl₃): δ 121.55, 73.61, 48.41, 29.91, 27.30, 27.06, 26.27, 26.00, 25.93, −1.78, −1.90;

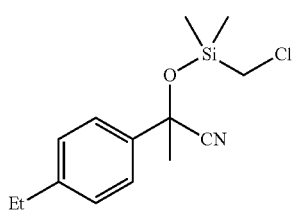

4aw

¹H NMR (400 MHz, CDCl₃): δ 7.31-7.05 (dd, 4H), 2.90 (dd, 1H), 2.60 (q, 3H), 1.82 (s, 3H), 1.25 (t, 3H), 0.30 (s, 3H); ¹³C NMR (100 MHz, CDCl₃): δ 143.43, 137.34, 127.08, 123.79, 123.36, 72.39, 31.71, 27.82, 21.02, 13.19, −1.62.

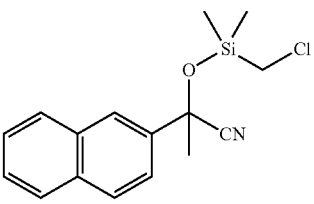

4aaa

¹H NMR (400 MHz, CDCl₃): δ 8.18 (s, 1H), 8.05-7.95 (m, 2H), 7.54-7.42 (m, 4H), 5.48 (s, 1H), 2.85 (dd, 1H), 0.31 (s, 6H); ¹³C NMR (100 MHz, CDCl₃): δ 138.44, 133.41, 132.87, 129.10, 128.49, 127.78, 127.05, 126.96, 123.90, 122.16, 121.35, 72.34, 33.28, 29.72, −2.06, −2.13;

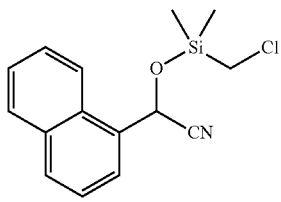
4aab

¹H NMR (400 MHz, CDCl₃): δ 8.05 (s, 1H), 7.91-7.85 (m, 3H), 7.60 (m, 1H), 7.55-7.53 (m, 2H), 2.80 (dd, 1H), 1.97 (s, 3H), 0.31 (s, 6H); ¹³C NMR (100 MHz, CDCl₃): δ 136.00, 132.47, 130.51, 128.89, 128.45, 128.25, 127.61, 127.25, 127.01, 122.81, 118.37, 60.96, 28.43, −1.96;

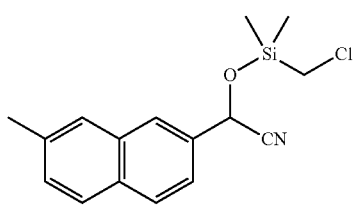
4aac

¹H NMR (400 MHz, CDCl₃): δ 8.05-7.95 (m, 2H), 7.51-7.43 (m, 4H), 5.50 (s, 1H), 2.80 (dd, 1H), 2.45 (s, 3H), 0.31 (s, 6H); ¹³C NMR (100 MHz, CDCl₃): δ 136.72, 134.82, 134.15, 133.63, 129.61, 128.29, 127.93, 127.65, 121.64, 119.02, 117.08, 61.42, 28.43, 21.71, −1.86;

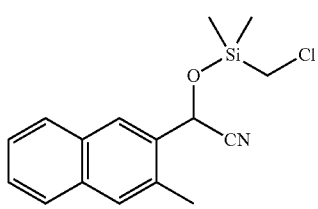
4aad

¹H NMR (400 MHz, CDCl₃): δ 8.08 (s, 1H), 7.99-7.93 (m, 2H), 7.38 (s, 1H), 7.05-6.99 (m, 2H), 2.83 (dd, 2H), 2.46 (s, 3H), 1.87 (s, 3H), 0.21 (s, 6H); ¹³C NMR (100 MHz, CDCl₃): δ 137.13, 134.15, 133.36, 133.04, 128.78, 128.22, 126.76, 126.20, 126.02, 122.72, 117.76, 60.00, 28.43, 20.35, −1.86;

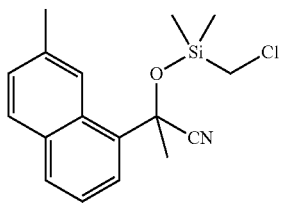
4aae

¹H NMR (400 MHz, CDCl₃): δ 8.05 (s, 1H), 7.91-7.85 (m, 3H), 7.60 (m, 1H), 7.55-7.53 (m, 2H), 2.80 (dd, 1H), 1.97 (s, 3H), 0.31 (s, 6H); ¹³C NMR (100 MHz, CDCl₃): δ 135.61, 134.64, 133.51, 131.21, 130.41, 127.93, 127.71, 127.47, 126.98, 124.99, 124.59, 70.29, 30.63, 21.71, 21.02, −0.62;

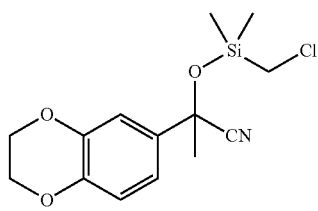
4aaf

¹H NMR (400 MHz, CDCl₃): δ 7.18 (s, 1H), 6.82 (dd, 2H), 4.48-4.34 (m, 4H), 2.85 (dd, 1H), 1.85 (s, 3H), 0.31 (s, 6H); ¹³C NMR (100 MHz, CDCl₃): δ 149.53, 143.03, 126.95, 123.36, 121.49, 117.25, 110.05, 71.70, 61.57, 31.71, 21.02, −1.62;

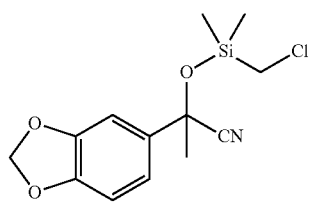
4aag

¹H NMR (400 MHz, CDCl₃): δ 6.99 (d, 2H), 6.87 (s, 1H), 5.97 (s, 2H), 2.72 (s, 2H), 2.14 (s, 3H), 0.21 (s, 6H); ¹³C NMR (100 MHz, CDCl₃): δ 151.58, 147.84, 132.17, 123.36, 123.13, 111.80, 104.82, 101.95, 71.70, 31.71, 21.02, −2.02;

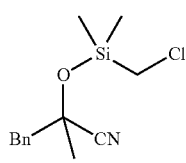
4aah

¹H NMR (400 MHz, CDCl₃): δ 7.40-7.29 (m, 5H), 4.21 (s, 1H), 3.30 (dd, 2H), 2.98 (dd, 2H), 1.70 (m, 2H), 0.23 (s, 6H); ¹³C NMR (100 MHz, CDCl₃): δ 136.86, 131.37, 128.99, 126.52, 108.38, 71.73, 43.63, 28.27, 21.02, −0.62;

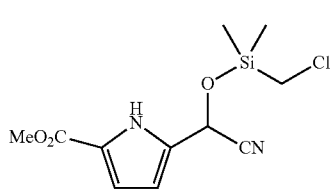
4aai

¹H NMR (400 MHz, CDCl₃): δ 7.17 (d, 1H), 5.89 (d, 1H), 5.54 (s, 1H), 5.46 (s, 1H), 3.89 (s, 3H), 2.89 (dd, 2H), 0.27 (s, 6H); ¹³C NMR (100 MHz, CDCl₃): δ 162.06, 133.50, 123.31, 113.36, 112.44, 107.34, 58.24, 52.08, 28.43, −1.76;

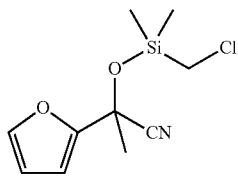

4aaj

¹H NMR (400 MHz, CDCl₃): δ 7.67 (d, 1H), 6.47-6.39 (m, 2H), 2.89 (dd, 2H), 1.88 (s, 3H), 0.23 (s, 6H); ¹³C NMR (100 MHz, CDCl₃): δ 158.66, 142.80, 118.78, 112.07, 105.96, 74.67, 29.37, 21.02, −1.62;

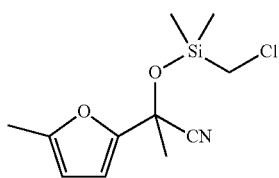

4aak

¹H NMR (400 MHz, CDCl₃): δ 6.27-6.03 (m, 2H), 2.83 (dd, 2H), 2.30 (dd, 3H), 1.86 (s, 3H), 0.23 (s, 6H); ¹³C NMR (100 MHz, CDCl₃): δ 158.49, 155.72, 118.78, 109.82, 108.25, 75.26, 29.37, 21.02, 14.79, −1.66;

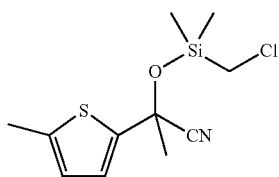

4aal

¹H NMR (400 MHz, CDCl₃): δ 6.57-6.53 (m, 2H), 2.84 (dd, 2H), 2.36 (s, 3H), 1.88 (s, 3H), 0.21 (s, 6H); ¹³C NMR (100 MHz, CDCl₃): δ 142.28, 142.06, 126.40, 120.85, 114.09, 79.52, 30.74, 21.02, 17.13, −1.62;

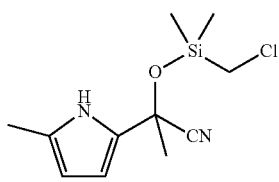

4aam

¹H NMR (400 MHz, CDCl₃): δ 5.57-5.53 (m, 2H), 5.03 (s, 1H), 2.54 (dd, 2H), 2.16 (s, 3H), 1.80 (s, 3H), 0.19 (s, 6H); ¹³C NMR (100 MHz, CDCl₃): δ 139.22, 132.45, 123.36, 106.96, 105.88, 70.68, 30.20, 21.02, 13.43, −1.52;

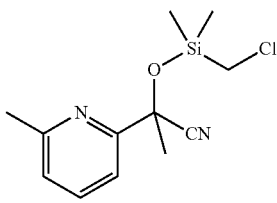

4aan

¹H NMR (400 MHz, CDCl₃): δ 7.95-7.53 (m, 3H), 2.73 (s, 3H), 2.84 (dd, 2H), 2.56 (s, 3H), 1.87 (s, 3H), 0.19 (s, 6H); ¹³C NMR (100 MHz, CDCl₃): δ 160.63, 156.83, 140.70, 124.71, 123.91, 119.14, 69.32, 29.74, 24.29, 21.02, −0.62;

4aao

¹H NMR (400 MHz, CDCl₃): 7.32-7.28 (m, 2H), 7.23-7.19 (m, 3H), 2.90-2.78 (m, 4H), 2.08-2.04 (m, 2H), 1.66 (s, 3H), 0.40 (s, 6H); ¹³C NMR (100 MHz, CDCl₃): δ 140.51, 128.67, 128.43, 126.35, 121.59, 69.92, 45.04, 30.74, 29.81, 29.02, −1.73, −1.82;

4aap

¹H NMR (400 MHz, CDCl₃): δ 8.39 (s, 1H), 7.85-7.53 (dd, 2H), 2.84 (dd, 2H), 2.33 (s, 3H), 1.88 (s, 3H), 0.21 (s, 6H); ¹³C NMR (100 MHz, CDCl₃): δ 156.16, 148.39, 132.96, 131.39, 123.91, 117.27, 69.17, 29.74, 21.02, 18.43, −1.62;

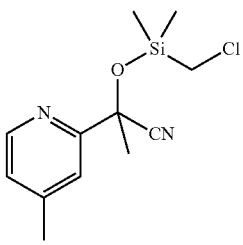

4aaq

¹H NMR (400 MHz, CDCl₃): δ 8.49 (d, 1H), 7.87 (s, 1H), 7.53 (d, 1H), 2.94 (dd, 2H), 2.36 (s, 3H), 1.87 (s, 3H), 0.22 (s, 6H); ¹³C NMR (100 MHz, CDCl₃): δ 157.81, 149.77, 147.81, 125.60, 123.91, 118.49, 68.85, 29.74, 21.23, 21.02, −1.72;

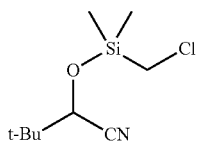

4aar

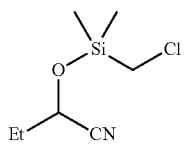

4aas

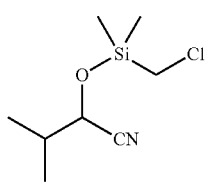

4aat

¹H NMR (400 MHz, CDCl₃): δ 4.26 (s, 1H), 2.97 (dd, 2H), 0.94 (s, 9H), 0.23 (s, 6H); ¹³C NMR (100 MHz, CDCl₃): δ 121.84, 73.83, 34.39, 28.43, 27.08, −1.86;

¹H NMR (400 MHz, CDCl₃): δ 4.22 (s, 1H), 2.98 (dd, 2H), 1.85 (q, 2H), 0.90 (t, 3H), 0.22 (s, 6H); ¹³C NMR (100 MHz, CDCl₃): δ 119.12, 64.40, 28.43, 26.00, 10.41, −1.86;

¹H NMR (400 MHz, CDCl₃): δ 4.21 (d, 1H), 2.98 (dd, 2H), 1.90 (m, 2H), 0.90 (d, 6H), 0.22 (s, 6H); ¹³C NMR (100 MHz, CDCl₃): δ 118.35, 69.93, 37.79, 28.43, 18.42, −1.86;

4) Nucleophilic Addition Reaction of Functionalized Silyl Cyanide 1aaa with Imines (Table 4).

Scheme (IIb)

General procedure 4: a catalyst I' (0.1 mmol), imine 3b (1.0 mmol) and a corresponding solvent (1 mL) were added into a dry Schlenk tube (25 mL). The mixture was added with 1aaa (2.0 mmol) after being stirred at the corresponding temperature for 0.5 h. The progress of the reaction was monitored by TLC analysis. After full consumption of the raw material 3b, 4b as shown in Scheme (IIb) was obtained by conventional post-treatment followed by column chromatography, or by column chromatography directly.

The specific experimental operations of the examples 116-159 are referred to general procedure 4. The specific reaction conditions and yields of each example are shown in Table 4.

TABLE 4

Specific reaction conditions and yields of the examples 116-159.

| Example | R² | R³ | PG | Catalyst I' (ml %) | Solvent | Temperature (° C.) | Product/Yield (%)/Ee (%) |
|---|---|---|---|---|---|---|---|
| 116 | C₆H₅ | H | Bn | DMAP (25) | CH₃CN | 25 | 4ba/79/— |
| 117 | C₆H₅ | H | CBz | DMAP (2.5) | toluene | 25 | 4bb/86/— |
| 118 | C₆H₅ | H | Ts | DMAP (2.5) | CH₂Cl₂ | 25 | 4bc/88/— |
| 119 | C₆H₅ | H | Boc | DMAP (2.5) | CH₂Cl₂ | 25 | 4bd/93/— |
| 120 | C₆H₅ | H | PMP | DMAP (15) | CH₃CN | 25 | 4be/82/— |
| 121 | C₆H₅ | H | P(O)Ph₂ | DMAP (5) | toluene | 25 | 4bf/90/— |
| 122 | C₆H₅ | H | PMP | DMAP (15) | CH₂Cl₂ | 25 | 4bg/89/— |
| 123 | C₆H₅ | CONMe₂ | PMP | DMAP (50) | CH₂Cl₂ | 25 | 4bh/86/— |
| 124 | C₆H₅ | CONEt₂ | PMP | DMAP (50) | THF | 50 | 4bi/88/— |
| 125 | C₆H₅ | Me | PMP | KOAc (15) | CH₃CN | 50 | 4bj/85/— |
| 126 | C₆H₅ | CO₂Me | PMP | KOAc (25) | toluene | 25 | 4bk/89/— |
| 127 | C₆H₅ | CO₂Et | PMP | K₂CO₃ (25) | CH₂Cl₂ | 25 | 4bl/87/— |
| 128 | C₆H₅ | CO₂t—Bu | PMP | K₂CO₃ (25) | CH₂Cl₂ | 50 | 4bm/78/— |
| 129 | C₆H₅ | CO₂Bn | PMP | K₂CO₃ (25) | CH₃CN | 25 | 4bn/89/— |
| 130 | 4-Cl—C₆H₄ | H | Ts | Et₃N (15) | THF | 40 | 4bo/87/— |
| 131 | 3-Cl—C₆H₄ | H | Ts | (i-Pr)₂NEt (25) | toluene | 50 | 4bp/83/— |
| 132 | 2-Cl—C₆H₄ | H | Ts | Et₃N (15) | CH₂Cl₂ | 55 | 4bq/87/— |
| 133 | 4-F—C₆H₄ | H | Ts | Et₃N (15) | CH₂Cl₂ | 25 | 4br/85/— |
| 134 | 4-Br—C₆H₄ | H | Ts | (i-Pr)₂NEt (25) | CH₃CN | 25 | 4bs/82/— |

TABLE 4-continued

Specific reaction conditions and yields of the examples 116-159.

| Example | R² | R³ | PG | Catalyst I' (ml %) | Solvent | Temperature (°C) | Product/ Yield (%)/ Ee (%) |
|---|---|---|---|---|---|---|---|
| 135 | 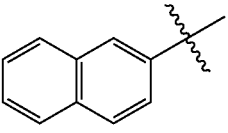 [SMILES: *c1ccc2ccccc2c1] | H | Ts | 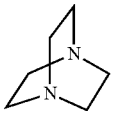 DABCO (5) | toluene | 50 | 4bt/95/— |
| 136 | 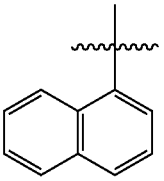 [SMILES: *c1cccc2ccccc12] | H | Ts | DMAP (5) | CH₂Cl₂ | 25 | 4bu/85/— |
| 137 | 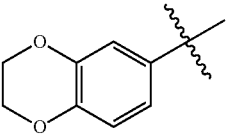 [SMILES: *c1ccc2c(c1)OCCO2] | H | Ts | DMAP (5) | CH₂Cl₂ | 50 | 4bv/80/— |
| 138 | 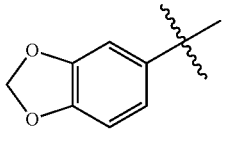 [SMILES: *c1ccc2c(c1)OCO2] | H | Ts | DMAP (5) | CH₃CN | 25 | 4bw/89/— |
| 139 | Bn | H | PMP | ZnI₂ (0.5) | CH₂Cl₂ | 0 | 4bx/82/— |
| 140 | BnCH₂ | H | PMP | TiCl₄ (2.5) | CH₂Cl₂ | 0 | 4by/87/— |
| 141 | Cy | H | PMP | Et₃N (5) | CH₂Cl₂ | 0 | 4bz/92/— |
| 142 | C₆H₅ | H | Bn | IC3 (20) | CH₃CN | −20 | 4ba/83/75 |
| 143 | C₆H₅ | H | CBz | IC3 (5) | toluene | −20 | 4bb/96/90 |
| 144 | C₆H₅ | H | Ts | IC3 (10) | CH₂Cl₂ | −20 | 4bc/89/94 |
| 145 | C₆H₅ | H | Boc | IC3 (5) | CH₂Cl₂ | −20 | 4bd/93/93 |
| 146 | C₆H₅ | H | PMP | IC3 (10) | CH₂Cl₂ | −20 | 4be/86/87 |
| 147 | C₆H₅ | H | P(O)Ph₂ | IC3 (20) | CH₂Cl₂ | −20 | 4bf/80/88 |
| 148 | 4-Cl—C₆H₄ | H | Ts | IC3 (10) | CH₂Cl₂ | −20 | 4bo/92/93 |
| 149 | 3-Cl—C₆H₄ | H | Ts | IC3 (10) | CH₂Cl₂ | −20 | 4bp/95/84 |
| 150 | 2-Cl—C₆H₄ | H | Ts | IC3 (10) | CH₂Cl₂ | −20 | 4bq/87/82 |
| 151 | 4-F—C₆H₄ | H | Ts | IC3 (10) | CH₂Cl₂ | −20 | 4br/84/94 |
| 152 | 4-Br—C₆H₄ | H | Ts | IC3 (10) | CH₂Cl₂ | −20 | 4bs/86/93 |
| 153 | 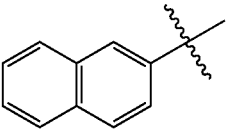 [SMILES: *c1ccc2ccccc2c1] | H | Ts | IC3 (10) | CH₂Cl₂ | −20 | 4bt/94/95 |
| 154 | 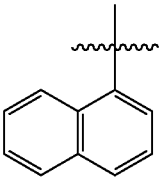 | H | Ts | IC3 (10) | CH₂Cl₂ | −20 | 4bu/95/82 |

TABLE 4-continued

Specific reaction conditions and yields of the examples 116-159.

| Example | R² | R³ | PG | Catalyst I' (ml %) | Solvent | Temperature (° C.) | Product/ Yield (%)/ Ee (%) |
|---|---|---|---|---|---|---|---|
| 155 | 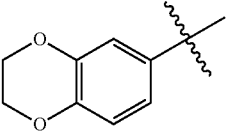 [SMILES: *c1ccc2c(c1)OCCO2] | H | Ts | IC3 (10) | CH₂Cl₂ | −20 | 4bv/90/90 |
| 156 | 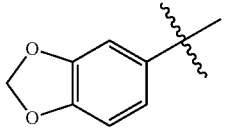 [SMILES: *c1ccc2c(c1)OCO2] | H | Ts | IC3 (10) | CH₂Cl₂ | −20 | 4bw/89/91 |
| 157 | Bn | H | PMP | IC3 (20) | CH₂Cl₂ | −20 | 4bx/80/68 |
| 158 | BnCH₂ | H | PMP | IC3 (20) | CH₂Cl₂ | −20 | 4by/90/75 |
| 159 | Cy | H | PMP | IC3 (20) | CH₂Cl₂ | −20 | 4bz/92/90 |

Products 4ba-4bz are known compounds. The characterizations of the products 4ba, 4be are consistent with the literature (*Chem. Comm.* 2009, 34, 5180); the characterizations of the products 4bb, 4bd are consistent with the literature (*Org. Lett.* 2012, 14, 882); the characterizations of the products 4bc, 4bj, 4bo, 4br, 4bt, 4bu, 4bw, 4bx, 4bz are consistent with the literature (*Angew. Chem. Int. Ed.* 2007, 46, 8468); the characterization of the product 4bf is consistent with the literature (*J. Am. Chem. Soc.* 2009, 131, 15118); the characterizations of the products 4bg, 4by are consistent with the literature (*Tetrahedron Lett.* 2012, 53, 1075); the characterizations of the products 4bh, 4bi, 4bk, 4bl, 4bm, 4bn are consistent with the literature (*Angew. Chem. Int. Ed.* 2015, 54, 13655); the characterizations of the products 4 bp, 4bv are consistent with the literature (*Tetrahedron Lett.* 2004, 45, 9565); and the characterizations of the products 4bq, 4bs, 4bx are consistent with the literature (*Tetrahedron Lett.* 2014, 55, 232).

5) Addition Reaction of the Functionalized Silyl Cyanide 1aaa with an Electron-Deficient Olefin (Table 5).

Scheme (IIc)

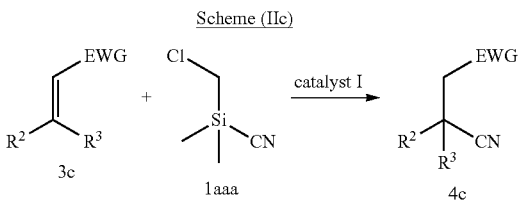

General procedure 5: the catalyst I (0.1 mmol), an electron-deficient olefin 3c (1.0 mmol) and a corresponding solvent (1 mL) were added into a dry Schlenk tube (25 mL). The mixture was added with the 1aaa (2.0 mmol) after being stirred at a corresponding temperature for 0.5 h. The progress of the reaction was monitored by TLC analysis. After the consumption of the raw material 3c was complete, 4c as shown in Scheme (IIc) was obtained by conventional post-treatment followed by column chromatography, or by column chromatography directly.

The specific experimental operations of the examples 160-182 are referred to general procedure 5. The specific reaction conditions and yield of each example are shown in Table 5.

TABLE 5

Specific reaction conditions and yields of the examples 160-182.

| Example | R² | R³ | EWG | Catalyst I (ml %) | Solvent | Temperature (° C.) | Product/ Yield (%)/Ee (%) |
|---|---|---|---|---|---|---|---|
| 160 | C₆H₅ | H | NO₂ | DMAP (25) | CH₃CN | 25 | 4ca/79/— |
| 161 | C₆H₅ | H | CO₂Me | DMAP (2.5) | toluene | 25 | 4cb/86/— |
| 162 | C₆H₅ | H | CONMe₂ | DMAP (15) | CH₃CN | 25 | 4cc/82/— |
| 163 | 4-Cl—C₆H₄ | H | NO₂ | Et₃N (15) | THF | 40 | 4cd/87/— |
| 164 | 3-NO₂—C₆H₄ | H | NO₂ | (i-Pr)₂NEt (25) | toluene | 50 | 4ce/83/— |
| 165 | 2-Cl—C₆H₄ | H | NO₂ | Et₃N (15) | CH₂Cl₂ | 55 | 4cf/87/— |
| 166 | 4-NO₂—C₆H₄ | H | NO₂ | Et₃N (15) | THF | 40 | 4cg/87/— |

TABLE 5-continued

Specific reaction conditions and yields of the examples 160-182.

| Example | $R^2$ | $R^3$ | EWG | Catalyst I (ml %) | Solvent | Temperature (° C.) | Product/ Yield (%)/Ee (%) |
|---|---|---|---|---|---|---|---|
| 167 | 4-OMe—$C_6H_4$ | H | $NO_2$ | $Et_3N$ (15) | THF | 40 | 4ch/87/— |
| 168 | 4-F—$C_6H_4$ | H | $NO_2$ | $Et_3N$ (15) | THF | 40 | 4ci/89/— |
| 169 | Cy | H | $NO_2$ | $Et_3N$ (5) | $CH_2Cl_2$ | 0 | 4cj/92/— |
| 170 | Ph | Me | $NO_2$ | $Et_3N$ (25) | $CH_2Cl_2$ | 70 | 4ck/86/— |
| 171 | Ph | $CF_3$ | $NO_2$ | $Et_3N$ (25) | $CH_2Cl_2$ | 30 | 4cl/80/— |
| 172 | $C_6H_5$ | H | $NO_2$ | IC1 ($R^4$ = OEt) | toluene | −20 | 4ca/79/85 |
| 173 | $C_6H_5$ | H | $CO_2Me$ | IC1 ($R^4$ = OEt) | toluene | −20 | 4cb/86/80 |
| 174 | $C_6H_5$ | H | $CONMe_2$ | IC1 ($R^4$ = OEt) | toluene | −20 | 4cc/82/68 |
| 175 | 4-Cl—$C_6H_4$ | H | $NO_2$ | IC1 ($R^4$ = OEt) | THF | −20 | 4cd/87/88 |
| 176 | 3-$NO_2$—$C_6H_4$ | H | $NO_2$ | IC1 ($R^4$ = OEt) | toluene | −20 | 4ce/83/87 |
| 177 | 2-Cl—$C_6H_4$ | H | $NO_2$ | IC1 ($R^4$ = OEt) | $CH_2Cl_2$ | −20 | 4cf/87/80 |
| 178 | 4-$NO_2$—$C_6H_4$ | H | $NO_2$ | IC1 ($R^4$ = OEt) | THF | −20 | 4cg/87/86 |
| 179 | 4-OMe—$C_6H_4$ | H | $NO_2$ | IC1 ($R^4$ = OEt) | THF | −20 | 4ch/87/88 |
| 180 | Cy | H | $NO_2$ | IC1 ($R^4$ = OEt) | $CH_2Cl_2$ | −20 | 4cj/92/87 |
| 181 | Ph | Me | $NO_2$ | IC1 ($R^4$ = OEt) | $CH_2Cl_2$ | 20 | 4ck/90/70 |
| 182 | Ph | $CF_3$ | $NO_2$ | IC1 ($R^4$ = OEt) | $CH_2Cl_2$ | −20 | 4cl/80/85 |

Products 4ca-4cl are known compounds. The characterizations of the compounds 4ca, 4cd-h are consistent with the literature (*Tetrahedron Lett.* 2009, 50, 640); the characterization of the compound 4cb is consistent with the literature (*Org. Biomol. Chem.* 2010, 8, 533); the characterization of the compound 4cj is consistent with the literature (*Org. Lett.* 2008, 10, 4141); the characterization of the compound 4ck is consistent with the literature (*Chem. Eur.* 12015, 21, 1280); and the characterization of the compound 4cl is consistent with the literature (*RSC Adv.* 2016, 6, 29977).

6) Nucleophilic Addition Reaction of Different Functionalized Silyl Cyanide 1a with Ketone 3Aao (Table 6).

Scheme (IId)

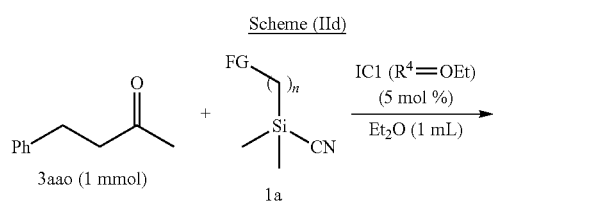

General procedure 6: a catalyst IC1 ($R^4$=OEt) (0.05 mol), ketone 3aao (1 mmol) and $Et_2O$ (1 mL) were added into a dry Schlenk tube (25 mL). The mixture was added with 1a after being stirred at a corresponding temperature for 0.5 h. The progress of the reaction was monitored by TLC analysis. After the consumption of the raw material 3aao was complete, 4d as shown in Scheme (IId) was obtained by conventional post-treatment followed by column chromatography, or by column chromatography directly, wherein, the compound 4d is in R or S configuration.

The specific experimental operations of the examples 183-199 are referred to general procedure 6. The specific reaction conditions and yield of each example are shown in Table 6.

TABLE 6

Specific reaction conditions and yields of the examples 183-199.

| Example | 1a (mmol) | Temperature (° C.) | Product/ Yield (%)/Ee (%) |
|---|---|---|---|
| 183 | 1aab (1.0) | −30 | 4da/76/95 |
| 184 | 1aab (1.2) | −30 | 4da/89/95 |
| 185 | 1aab (1.5) | −30 | 4da/95/95 |
| 186 | 1aab (1.75) | −30 | 4da/96/95 |
| 187 | 1aab (2.0) | −30 | 4da/96/95 |
| 188 | 1aab (2.5) | −30 | 4da/97/93 |
| 189 | 1aab (3.0) | −30 | 4da/98/90 |
| 190 | 1aba (1.5) | −40 | 4db/96/93 |
| 191 | 1aea (1.5) | 0 | 4dc/79/85 |
| 192 | 1aeb (1.5) | 0 | 4dd/87/88 |
| 193 | 1abc (1.5) | −10 | 4de/89/94 |
| 194 | 1aec (1.5) | 10 | 4df/91/87 |
| 195 | 1abd (1.5) | −20 | 4dg/96/96 |
| 196 | 1abc (1.5) | −40 | 4dh/89/95 |
| 197 | 1aca (1.5) | −20 | 4di/88/90 |
| 198 | 1ada (1.5) | −10 | 4dj/92/90 |
| 199 | 1adb (1.5) | −20 | 4dk/94/94 |

The characterizations of 4da-4dk are as follows:

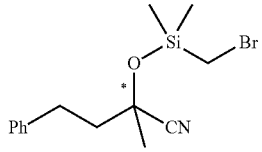
4da

¹H NMR (400 MHz, CDCl₃): 7.42-7.29 (m, 2H), 7.29-7.19 (m, 3H), 2.60-2.48 (m, 4H), 2.08-2.04 (m, 2H), 1.67 (s, 3H), 0.40 (s, 6H); ¹³C NMR (100 MHz, CDCl₃): δ 140.55, 128.17, 128.33, 126.45, 121.79, 69.82, 45.44, 30.84, 30.91, 29.12, −1.75, −1.86;

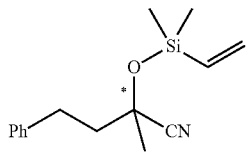
4db

¹H NMR (400 MHz, CDCl₃): 7.41-7.30 (m, 2H), 7.26-7.17 (m, 3H), 5.30 (dd, 1H), 5.22-5.17 (m, 2H), 2.55-2.48 (m, 2H), 2.08-2.04 (m, 2H), 1.68 (s, 3H), 0.42 (s, 6H); ¹³C NMR (100 MHz, CDCl₃): δ 143.84, 140.87, 128.91, 128.43, 128.11, 126.57, 119.43, 69.88, 40.92, 33.90, 27.60, −1.78, −1.89;

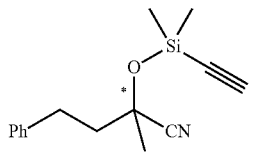
4dc

¹H NMR (400 MHz, CDCl₃): 7.47-7.32 (m, 2H), 7.26-7.17 (m, 3H), 2.81 (s, 1H), 2.55-2.48 (m, 2H), 2.08-2.04 (m, 2H), 1.68 (s, 3H), 0.42 (s, 6H); ¹³C NMR (100 MHz, CDCl₃): δ 140.87, 128.91, 128.43, 126.57, 119.43, 118.74, 70.41, 51.51, 40.92, 33.90, 27.60, −1.78, −1.89;

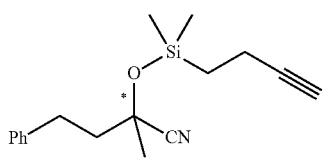
4dd

¹H NMR (400 MHz, CDCl₃): 7.47-7.32 (m, 2H), 7.26-7.17 (m, 3H), 2.83 (s, 1H), 2.56-2.47 (m, 4H), 1.70 (s, 3H), 1.25 (t, 2H), 0.42 (s, 6H); ¹³C NMR (100 MHz, CDCl₃): δ 140.87, 128.91, 128.43, 126.57, 119.43, 84.72, 68.96, 64.57, 40.92, 33.90, 27.60, 18.16, 12.42, −1.78, −1.89;

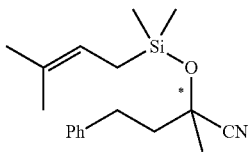
4de

¹H NMR (400 MHz, CDCl₃): δ 7.49-7.37 (m, 2H), 7.28-7.19 (m, 3H), 5.30 (t, 1H), 2.54 (t, 2H), 2.09 (t, 2H), 2.00 (d, 2H), 1.69 (s, 3H), 1.59 (s, 3H), 1.44 (s, 3H), 0.43 (s, 6H); ¹³C NMR (100 MHz, CDCl₃): δ 140.87, 128.91, 128.43, 127.89, 126.57, 119.83, 119.43, 68.96, 40.92, 33.90, 27.60, 25.15, 18.07, 14.78, −1.77, −1.88;

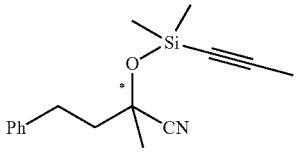
4df

¹H NMR (400 MHz, CDCl₃): δ 7.55-7.40 (m, 2H), 7.26-7.17 (m, 3H), 2.54 (t, 2H), 2.09 (t, 2H), 1.80 (s, 3H), 1.69 (s, 3H), 0.42 (s, 6H); ¹³C NMR (100 MHz, CDCl₃): δ 140.87, 128.91, 128.43, 126.57, 119.43, 103.01, 79.50, 70.41, 40.92, 33.90, 27.60, 7.11, −1.78, −1.89;

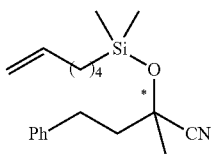
4dg

¹H NMR (400 MHz, CDCl₃): 7.41-7.30 (m, 2H), 7.26-7.17 (m, 3H), 5.97-5.80 (m, 1H), 5.17-5.19 (m, 2H), 2.57 (t, 2H), 2.49-2.15 (m, 4H), 1.81 (m, 2H), 1.39-1.25 (m, 4H), 1.15-1.08 (m, 2H), 0.43 (s, 6H); ¹³C NMR (100 MHz, CDCl₃): δ 140.87, 138.80, 128.91, 128.43, 126.57, 119.43, 114.45, 68.96, 40.92, 35.17, 33.90, 29.94, 27.60, 23.57, 15.78, −1.77, −1.88;

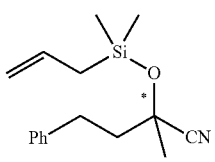
4dh

¹H NMR (400 MHz, CDCl₃): 7.41-7.30 (m, 2H), 7.26-7.17 (m, 3H), 5.70 (dd, 1H), 5.12-5.07 (m, 2H), 2.55-2.48 (m, 2H), 2.08-2.04 (m, 4H), 1.69 (s, 3H), 0.43 (s, 6H); ¹³C NMR (100 MHz, CDCl₃): δ 140.87, 135.46, 128.91, 128.43, 126.57, 119.43, 110.94, 68.96, 40.92, 33.90, 27.60, 23.11, −1.77, −1.88;

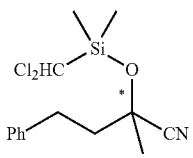
4di

¹H NMR (400 MHz, CDCl₃): 7.43-7.33 (m, 2H), 7.29-7.18 (m, 3H), 5.70 (s, 1H), 2.58-2.48 (m, 2H), 2.08-2.04 (m, 2H), 1.75 (s, 3H), 0.49 (s, 6H); ¹³C NMR (100 MHz, CDCl₃): δ 140.87, 128.91, 128.43, 126.57, 119.43, 69.17, 40.92, 33.90, 27.86, 17.56, −1.77, −1.88;

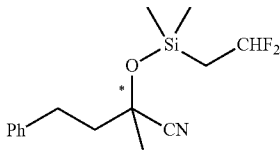
4dj

¹H NMR (400 MHz, CDCl₃): 7.42-7.29 (m, 2H), 7.29-7.19 (m, 3H), 5.30-5.17 (m, 1H), 2.54 (t, 4H), 2.08 (t, 2H), 1.69 (s, 3H), 1.48-1.40 (m, 2H), 0.43 (s, 6H); ¹³C NMR (100 MHz, CDCl₃): δ 140.87, 128.91, 128.43, 126.57, 119.43, 68.96, 50.36, 40.92, 33.90, 27.60, −1.75, −1.86;

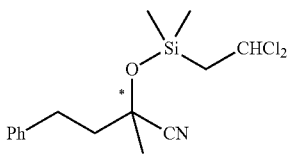
4dk

¹H NMR (400 MHz, CDCl₃): 7.43-7.30 (m, 2H), 7.24-7.15 (m, 3H), 5.40 (t, 1H), 2.55 (t, 4H), 2.07 (t, 2H), 1.69 (s, 3H), 1.58 (d, 2H), 0.44 (s, 6H); ¹³C NMR (100 MHz, CDCl₃): δ 140.87, 128.91, 128.43, 126.57, 119.43, 92.42, 69.76, 68.96, 40.92, 33.90, 27.60, −1.75, −1.86.

7) Tandem Nucleophilic Addition Reaction/Functional Group Transfer Reaction of the Functionalized Silyl Cyanide 1aa (Table 7)

Scheme (III)

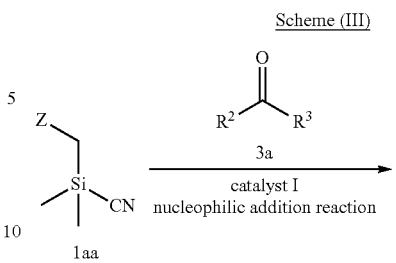

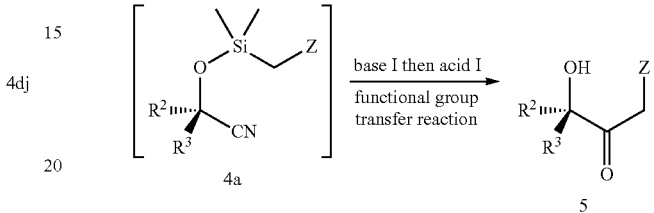

General procedure 7: the catalyst I, the raw material of 3a (1.0 mmol) and a corresponding solvent (1 mL) were added into a dry Schlenk tube (25 mL). The mixture was added with 1aa (1.5 mmol) after being stirred at a $T_1$ temperature for 0.5 h. The progress of the reaction was monitored by TLC analysis. After the consumption of the raw material 3a was complete, the crude product 4a was obtained by filtering the reaction mixture by 5 cm silica gel column, eluting with Et₂O, and removing solvent under reduced pressure. The crude product 4a was transferred to a dry Schlenk tube (25 mL) and dissolved with anhydrous THF (4.0 mL). The resulting solution was stirred at a $T_2$ temperature for 0.5 h, and base I was added dropwise slowly. The process of the reaction was monitored by TLC analysis. After the consumption of 4a was complete, the reaction was quenched by 5 mL acid I (4 M). The resulting mixture was extracted three times with EtOAc. Product 5 as shown in Scheme (III) was obtained by rotary evaporation of the solvent and column chromatography.

The specific experimental operations of the examples 200-241 are referred to general procedure 7. The specific reaction conditions and yield of each example are shown in Table 7.

TABLE 7

Specific reaction conditions and yields of the examples 200-241.

| Example | R²/R³/Z | Catalyst I (mol %) | Solvent | $T_1$ (° C.) | Base I (eq) $T_2$ (° C.) | Acid I | Product/ Yield (%)/ Ee (%) |
|---|---|---|---|---|---|---|---|
| 200 | BnCH₂/Me/Cl | Na₂CO₃ (5) | MeCN | 25 | LDA (1.2) −30 | Hydrochloric acid | 5a/68/— |
| 201 | BnCH₂/Me/Cl | Na₂CO₃ (5) | MeCN | 25 | LDA (1.5) −30 | Hydrochloric acid | 5a/80/— |
| 202 | BnCH₂/Me/Cl | Na₂CO₃ (5) | MeCN | 25 | LDA (2.0) −30 | Hydrochloric acid | 5a/78/— |
| 203 | BnCH₂/Me/Cl | Na₂CO₃ (5) | MeCN | 25 | LDA (3.0) −30 | Hydrochloric acid | 5a/75/— |
| 204 | BnCH₂/Me/Cl | Na₂CO₃ (5) | MeCN | 25 | LDA (1.5) −30 | Hydrochloric acid | 5a/65/— |
| 205 | BnCH₂/Me/Cl | Na₂CO₃ (5) | MeCN | 25 | LDA (1.5) −30 | Sulfuric acid | 5a/78/— |
| 206 | BnCH₂/Me/Cl | Na₂CO₃ (5) | MeCN | 25 | NaHMDS (1.5) −30 | Hydrochloric acid | 5a/38/— |

TABLE 7-continued

Specific reaction conditions and yields of the examples 200-241.

| Example | R²/R³/Z | Catalyst I (mol %) | Solvent | T₁ (° C.) | Base I (eq) T₂ (° C.) | Acid I | Product/Yield (%)/Ee (%) |
|---|---|---|---|---|---|---|---|
| 207 | BnCH₂/Me/Cl | Na₂CO₃ (5) | MeCN | 25 | LDA (1.5) −78 | Hydrochloric acid | 5a/66/— |
| 208 | BnCH₂/Me/Cl | Na₂CO₃ (5) | MeCN | 25 | LDA (1.5) −50 | Hydrochloric acid | 5a/75/— |
| 209 | BnCH₂/Me/Cl | Na₂CO₃ (5) | MeCN | 25 | LDA (1.5) 0 | Hydrochloric acid | 5a/68/— |
| 210 | BnCH₂/Me/Cl | Na₂CO₃ (5) | MeCN | 25 | LDA (1.5) 30 | Hydrochloric acid | 5a/39/— |
| 211 | BnCH₂/Et/Cl | K₂CO₃ (5) | MeCN | 25 | LDA (1.5) −30 | Hydrochloric acid | 5b/78/— |
| 212 | BnCH₂/i-Pr/Cl | K₂CO₃ (5) | MeCN | 50 | LDA (1.5) −30 | Hydrochloric acid | 5c/74/— |
| 213 | BnCH₂/(vinyl-substituted)/Cl | KOAc (25) | MeCN | 25 | LDA (1.5) −30 | Hydrochloric acid | 5d/68/— |
| 214 | BnCH₂/(alkynyl-substituted)/Cl | K₂CO₃ (15) | THF | 25 | LDA (1.5) −30 | Hydrochloric acid | 5e/57/— |
| 215 | 4-Cl—C₆H₄/Me/Cl | Et₃N (5) | THF | 40 | LDA (1.5) −30 | Hydrochloric acid | 5f/64/— |
| 216 | 4-Me—C₆H₄/Me/Cl | K₂CO₃ (25) | THF | 0 | LDA (1.5) −30 | Hydrochloric acid | 5g/75/— |
| 217 | 2-naphthyl/Me/Cl | DABCO (5) | THF | 50 | LDA (1.5) −30 | Hydrochloric acid | 5h/69/— |
| 218 | (1,4-benzodioxin-6-yl)/Me/Cl | DMAP (10) | MeCN | 25 | LDA (1.5) −30 | Hydrochloric acid | 5i/67/— |
| 219 | (1,3-benzodioxol-5-yl)/Me/Cl | KI (10) | MeCN | 25 | LDA (1.5) −30 | Hydrochloric acid | 5j/75/— |
| 220 | (2-furyl)/Me/Cl | TiCl₄ (0.5) | toluene | 0 | LDA (1.5) −30 | Hydrochloric acid | 5k/58/— |
| 221 | (5-methyl-2-furyl)/Me/Cl | ZnI₂ (0.5) | MeCN | 25 | LDA (1.5) −30 | Hydrochloric acid | 5l/60/— |
| 222 | Et/Me/Cl | Zn(OTf)₂ (1) | toluene | 25 | LDA (1.5) −30 | Hydrochloric acid | 5m/68/— |
| 223 | i-Pr/Me/Cl | Zn(OTf)₂ (1) | toluene | 25 | LDA (1.5) −30 | Hydrochloric acid | 5n/66/— |
| 224 | CyCH₂/Et/Cl | Zn(OTf)₂ (0.1) | MeCN | 25 | LDA (1.5) −30 | Hydrochloric acid | 5o/70/— |
| 225 | CyCH₂/Allyl/Cl | K₂CO₃ (1) | MeCN | 50 | LDA (1.5) −30 | Hydrochloric acid | 5p/48/— |

TABLE 7-continued

Specific reaction conditions and yields of the examples 200-241.

| Example | $R^2/R^3/Z$ | Catalyst I (mol %) | Solvent | $T_1$ (° C.) | Base I (eq) $T_2$ (° C.) | Acid I | Product/ Yield (%)/ Ee (%) |
|---|---|---|---|---|---|---|---|
| 226 | BnCH$_2$/Me/Cl | IC1 (10) (R$^4$ = OEt) | Et$_2$O | 25 | LDA (1.5) −30 | Hydrochloric acid | 5a/68/95 |
| 227 | BnCH$_2$/Et/Cl | IC1 (10) (R$^4$ = OEt) | MeCN | 25 | LDA (1.5) −30 | Hydrochloric acid | 5b/64/89 |
| 228 | BnCH$_2$/i-Pr/Cl | IC1 (10) (R$^4$ = OEt) | MeCN | 50 | LDA (1.5) −30 | Hydrochloric acid | 5c/58/78 |
| 229 | BnCH$_2$/vinyl/Cl | IC1 (10) (R$^4$ = OEt) | Et$_2$O | 25 | LDA (1.5) −30 | Hydrochloric acid | 5d/62/85 |
| 230 | BnCH$_2$/ethynyl/Cl | IC1 (20) (R$^4$ = OEt) | THF | 25 | LDA (1.5) −30 | Hydrochloric acid | 5e/58/87 |
| 231 | 4-Cl—C$_6$H$_4$/Me/Cl | IC1 (10) (R$^4$ = OEt) | THF | 40 | LDA (1.5) −30 | Hydrochloric acid | 5f/65/94 |
| 232 | 4-Me—C$_6$H$_4$/Me/Cl | IC4 (20) | THF | 0 | LDA (1.5) −30 | Hydrochloric acid | 5g/59/90 |
| 233 | 2-naphthyl/Me/Cl | IC1 (10) (R$^4$ = OEt) | THF | 50 | LDA (1.5) −30 | Hydrochloric acid | 5h/68/90 |
| 234 | 2,3-dihydrobenzo[1,4]dioxin-6-yl/Me/Cl | IC1 (10) (R$^4$ = OEt) | MeCN | 25 | LDA (1.5) −30 | Hydrochloric acid | 5i/72/89 |
| 235 | benzo[1,3]dioxol-5-yl/Me/Cl | IC1 (10) (R$^4$ = OEt) | CH$_2$Cl$_2$ | 25 | LDA (1.5) −30 | Hydrochloric acid | 5j/70/90 |
| 236 | furan-2-yl/Me/Cl | IC1 (10) (R$^4$ = OEt) | toluene | 0 | LDA (1.5) −30 | Hydrochloric acid | 5k/60/86 |
| 237 | 5-methylfuran-2-yl/Me/Cl | IC2 (10) (X$^1$ = NTf$_2$) | MeCN | 25 | LDA (1.5) −30 | Hydrochloric acid | 5l/58/80 |
| 238 | Et/Me/Cl | IC1 (10) (R$^4$ = OEt) | Et$_2$O | 25 | LDA (1.5) −30 | Hydrochloric acid | 5m/70/90 |
| 239 | i-Pr/Me/Cl | IC1 (10) (R$^4$ = OEt) | Et$_2$O | 25 | LDA (1.5) −30 | Hydrochloric acid | 5n/66/94 |
| 240 | CyCH$_2$/Et/Cl | IC1 (10) (R$^4$ = OEt) | Et$_2$O | 50 | LDA (1.5) −30 | Hydrochloric acid | 5o/65/85 |
| 241 | Cy/Allyl/Cl | IC1 (10) (R$^4$ = OEt) | Et$_2$O | 25 | LDA (1.5) −30 | Hydrochloric acid | 5p/58/95 |

The characterizations of 5a-5p are as follows:

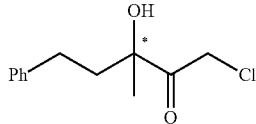
5a

¹H NMR (400 MHz, CDCl₃): 7.30-7.27 (m, 2H), 7.22-7.14 (m, 3H), 4.42 (dd, 1H), 4.39 (dd, 1H), 3.10 (s, br, 1H), 2.76-2.73 (m, 1H), 2.48-2.47 (m, 1H), 2.09-2.03 (m, 2H), 1.45 (s, 3H); $^{13}$C NMR (100 MHz, CDCl₃): δ 205.88, 140.88, 128.67, 128.43, 126.34, 79.43, 45.48, 41.90, 29.83, 26.16;

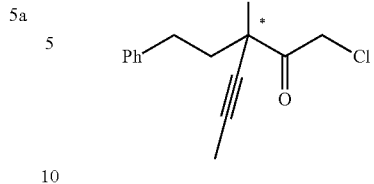
5e

¹H NMR (400 MHz, CDCl₃): 7.32-7.24 (m, 2H), 7.21-7.14 (m, 3H), 4.42 (dd, 1H), 4.39 (dd, 1H), 3.17 (s, br, 1H), 2.68-2.60 (m, 1H), 2.48-2.47 (m, 1H), 1.80 (s, 1H); $^{13}$C NMR (100 MHz, CDCl₃): δ 213.74, 140.87, 128.91, 128.43, 126.57, 75.70, 73.78, 69.54, 45.36, 39.10, 33.22, 7.30;

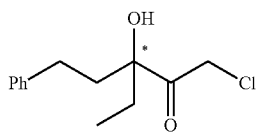
5b

¹H NMR (400 MHz, CDCl₃): 7.32-7.26 (m, 2H), 7.20-7.13 (m, 3H), 4.42 (dd, 1H), 4.39 (dd, 1H), 3.10 (s, br, 1H), 2.78-2.75 (m, 1H), 2.48-2.47 (m, 1H), 1.83 (q, 2H), 0.95 (t, 3H); $^{13}$C NMR (100 MHz, CDCl₃): δ 205.88, 140.88, 128.67, 128.43, 126.34, 79.43, 45.48, 41.90, 29.83, 26.16;

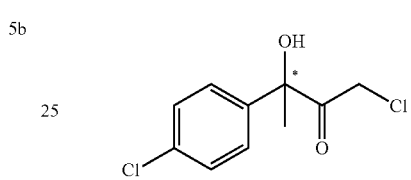
5f

¹H NMR (400 MHz, CDCl₃): 7.38 (m, 4H), 4.40 (dd, 1H), 4.32 (dd, 1H), 3.56 (s, br, 1H), 1.78 (s, 3H); $^{13}$C NMR (100 MHz, CDCl₃): δ 202.91, 139.26, 134.61, 129.13, 126.89, 80.16, 45.18, 26.14;

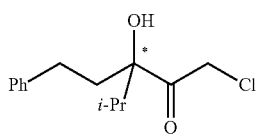
5c

¹H NMR (400 MHz, CDCl₃): 7.33-7.25 (m, 2H), 7.21-7.14 (m, 3H), 4.42 (dd, 1H), 4.39 (dd, 1H), 3.14 (s, br, 1H), 2.78-2.75 (m, 1H), 2.48-2.47 (m, 1H), 1.89-1.81 (q, 1H), 0.95 (d, 3H); $^{13}$C NMR (100 MHz, CDCl₃): δ 213.54, 140.87, 128.91, 128.43, 126.57, 85.61, 46.74, 33.13, 30.70, 27.81, 16.69;

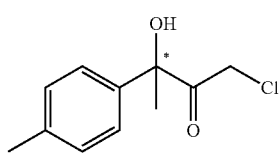
5g

¹H NMR (400 MHz, CDCl₃): 7.30-7.05 (m, 4H), 4.30 (dd, 1H), 4.22 (dd, 1H), 3.36 (s, br, 1H), 2.34 (s, 3H), 1.78 (s, 3H); $^{13}$C NMR (100 MHz, CDCl₃): δ 202.91, 139.26, 134.61, 129.13, 126.89, 80.16, 45.18, 26.14;

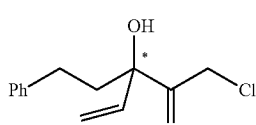
5d

¹H NMR (400 MHz, CDCl₃): 7.33-7.25 (m, 2H), 7.21-7.14 (m, 3H), 5.92 (dd, 1H), 5.30-5.05 (m, 1H), 4.42 (dd, 1H), 4.39 (dd, 1H), 3.16 (s, br, 1H), 2.78-2.75 (m, 1H), 2.48-2.47 (m, 1H); $^{13}$C NMR (100 MHz, CDCl₃): δ 207.22, 143.05, 140.87, 128.91, 128.43, 126.57, 118.08, 77.54, 46.08, 35.61, 32.84;

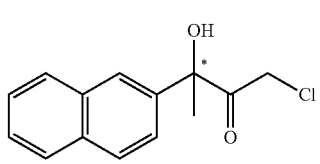
5h

¹H NMR (400 MHz, CDCl₃): 8.10-7.95 (m, 2H), 7.65-7.55 (m, 2H), 7.45 (s, 1H), 7.30 (d, 1H), 4.32 (dd, 1H), 4.25 (dd, 1H), 3.38 (s, br, 1H), 1.88 (s, 3H); $^{13}$C NMR (100 MHz, CDCl₃): δ 205.09, 146.27, 134.44, 134.11, 130.55, 129.46, 127.57 (d, J=6.1 Hz), 126.56 (d, J=18.2 Hz), 125.97, 79.45, 45.05, 24.85;

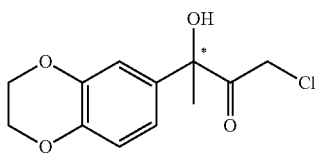
5i

¹H NMR (400 MHz, CDCl₃): 7.05 (s, 1H), 6.55 (s, 1H), 4.55 (s, 2H), 4.30 (s, 2H), 4.12 (dd, 1H), 4.05 (dd, 1H), 3.38 (s, br, 1H), 1.88 (s, 3H); ¹³C NMR (100 MHz, CDCl₃): δ 205.09, 147.89, 142.43, 128.97, 122.55, 121.74, 112.84, 79.08, 61.57, 45.05, 24.85;

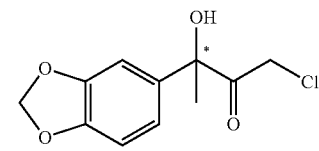
5j

¹H NMR (400 MHz, CDCl₃): 7.03 (s, 1H), 6.85 (s, 1H), 6.30 (s, 2H), 4.12 (dd, 1H), 4.05 (dd, 1H), 3.58 (s, br, 1H), 1.89 (s, 3H); ¹³C NMR (100 MHz, CDCl₃): δ 205.09, 148.50, 146.18, 135.49, 123.04, 116.17, 107.96, 101.95, 79.08, 45.05, 24.85;

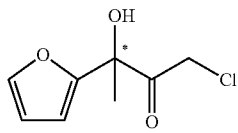
5k

¹H NMR (400 MHz, CDCl₃): 7.63 (d, 1H), 6.55 (dd, 1H), 6.39 (d, 1H), 4.10 (dd, 1H), 4.00 (dd, 1H), 3.54 (s, br, 1H), 1.69 (s, 3H); ¹³C NMR (100 MHz, CDCl₃): δ 214.78, 158.50, 142.80, 112.07, 105.50, 75.98, 45.28, 23.37;

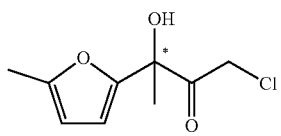
5l

¹H NMR (400 MHz, CDCl₃): 6.35 (d, 1H), 6.09 (dd, 1H), 4.10 (dd, 1H), 4.00 (dd, 1H), 3.54 (s, br, 1H), 1.69 (s, 3H); ¹³C NMR (100 MHz, CDCl₃): δ 214.78, 155.72, 150.21, 111.01, 108.25, 75.10, 45.28, 23.37, 14.79;

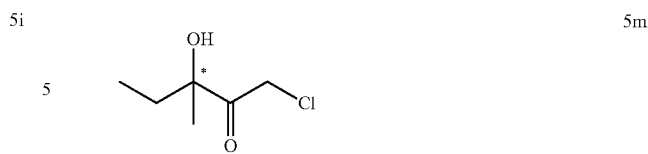
5m

¹H NMR (400 MHz, CDCl₃): 4.45 (dd, 2H), 2.97 (s, br, 1H), 1.81-1.67 (m, 2H), 1.39 (s, 3H), 0.86 (t, 3H); ¹³C NMR (100 MHz, CDCl₃): δ 206.00, 79.86, 45.73, 33.02, 25.44, 7.71;

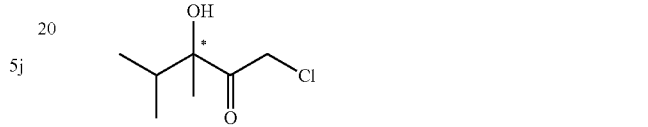
5n

¹H NMR (400 MHz, CDCl₃): 4.47 (dd, 1H), 4.43 (dd, 1H), 2.90 (s, br, 1H), 1.99-1.92 (m, 1H), 1.33 (s, 3H), 0.96 (dd, 1.2 Hz, 3H), 0.79 (d, 3H); ¹³C NMR (100 MHz, CDCl₃): δ 206.56, 81.69, 46.13, 35.49, 23.70, 17.08, 15.86;

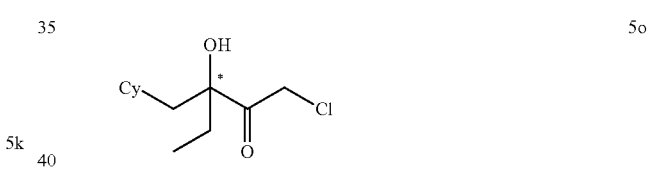
5o

¹H NMR (400 MHz, CDCl₃): 4.43 (dd, 1H), 4.37 (dd, 1H), 3.12 (s, br, 1H), 1.72-1.56 (m, 8H), 1.50-1.47 (m, 1H), 1.39-1.32 (m, 1H), 1.25-1.06 (m, 3H), 1.11-0.86 (m, 2H), 0.81 (t, 3H); ¹³C NMR (100 MHz, CDCl₃): δ 206.36, 82.67, 46.64, 46.06, 34.94, 34.39, 33.53, 33.36, 26.29, 26.27, 26.13, 7.49;

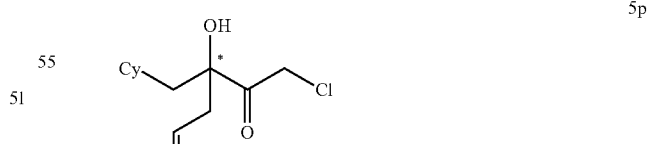
5p

¹H NMR (400 MHz, CDCl₃): 5.73-5.66 (m, 1H), 5.19-5.13 (m, 2H), 4.43 (s, 2H), 3.02 (s, 1H), 2.50-2.40 (m, 2H), 1.76-1.60 (m, 6H), 1.54-1.50 (m, 1H), 1.43-1.36 (m, 1H), 1.28-1.08 (m, 3H), 1.01-0.83 (m, 2H); ¹³C NMR (100 MHz, CDCl₃): δ 205.83, 131.52, 120.41, 82.10, 46.80, 46.55, 44.77, 34.88, 34.39, 34.47, 26.29, 26.26, 26.13.

8) Total Synthesis of the Colorado Potato Beetle Aggregation Pheromone (Table 8).

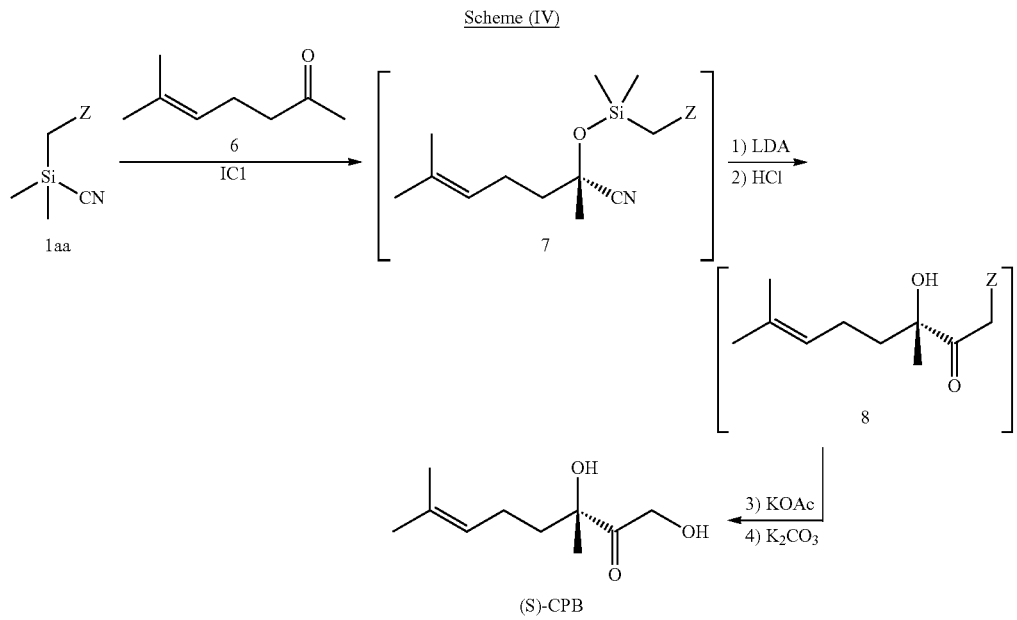

Scheme (IV)

General procedure 8: the catalyst IC1 (R is OEt), ketone 6 (40.0 mmol) and a corresponding solvent (40 mL) were added into a dry Schlenk tube (25 mL). After being stirred at −30° C. for 0.5 h, 1aa (60 mmol) was added to the mixture. The process of the reaction was monitored by TLC analysis. After the consumption of the raw material 6 was complete, crude product 7 was obtained by filtering the reaction mixture by 5 cm silica gel column, eluting with $Et_2O$, and removing the solvent under reduced pressure. Then the crude product 7 was transferred to a dry Schlenk tube (150 mL) and dissolved with anhydrous THF (40 mL). The mixture was stirred at −30° C. for 0.5 h, and then base LDA (60 mmol) was added dropwise slowly. The process of the reaction was monitored by TLC analysis. After the consumption of the raw material 7 was complete, the reaction mixture was quenched by 20 mL hydrochloric acid (4 M), and extracted three times by EtOAc. Crude 8 was obtained by combing the organic phase, and rotary evaporation of the solvent and dried under vacuum.

Then, the crude 8 was dissolved with tetrahydrofuran (40 mL), and then added KOAc (45 mmol). The mixture was refluxed at 100° C. and the process of the reaction was monitored by TLC analysis. After the 8 was converted completely, the reaction mixture was rotary evaporated to remove the solvent. Then saturated ammonium chloride (40 mL) and ethyl acetate (60 mL) was added for liquid separation, After phase separation, the aqueous phase was extracted with ethyl acetate (40 mL*2). The organic phase combined, dried with anhydrous sodium sulfate and rotary evaporated to remove the solvent to provide light brown oily liquid.

Next, the light brown oily liquid was dissolved in methanol (40 mL), and added $K_2CO_3$ (45 mmol) while stirring. The resulting solution was heated to reflux at 100° C. oil bath until the corresponding intermediate was converted completely by TLC analysis. The reaction mixture was then rotary evaporated to remove MeOH under reduced pressure. Saturated ammonium chloride (40 mL) and ethyl acetate (60 mL) were added. After phase separation, the aqueous phase was extracted with ethyl acetate (20 mL*2). The organic phase was combined and dried with anhydrous sodium sulfate. After rotary evaporation of the solvent, the resulted light brown oily liquid was subjected to column chromatography to afford pure(S)—CPB as shown in (IV).

The specific experimental operations of the examples 242-243 are referred to general procedure 8. The specific reaction conditions and yield of each example are shown in Table 8.

TABLE 8

Specific reaction conditions and yields of the example 242-243.

| Example | Z | Yield (%) | Ee (%) |
|---|---|---|---|
| 242 | Cl | 65 | 97 |
| 243 | Br | 53 | 96 |

The characterization of(S)—CPB is as follows:

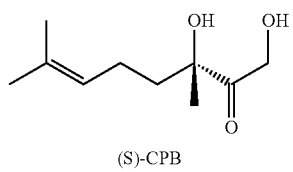

(S)-CPB $^1$H NMR (400 MHz, $CDCl_3$): 5.04 (t, 1H), 4.54-4.43 (m, 2H), 2.94 (s, br, 2H), 2.14-2.05 (m, 1H), 1.95-1.87 (m, 1H), 1.83-1.71 (m, 2H), 1.67 (s, 3H), 1.58 (s, 3H), 1.37 (s, 3H); $^{13}$C NMR (100 MHz, $CDCl_3$): δ 214.25, 133.39, 123.07, 78.58, 64.76, 40.03, 26.20, 25.71, 22.26, 17.76;

9) Tandem Cyanosilylation Reaction/Ring-Closing Olefin Metathesis of Cyansilane Lab (Table 9).

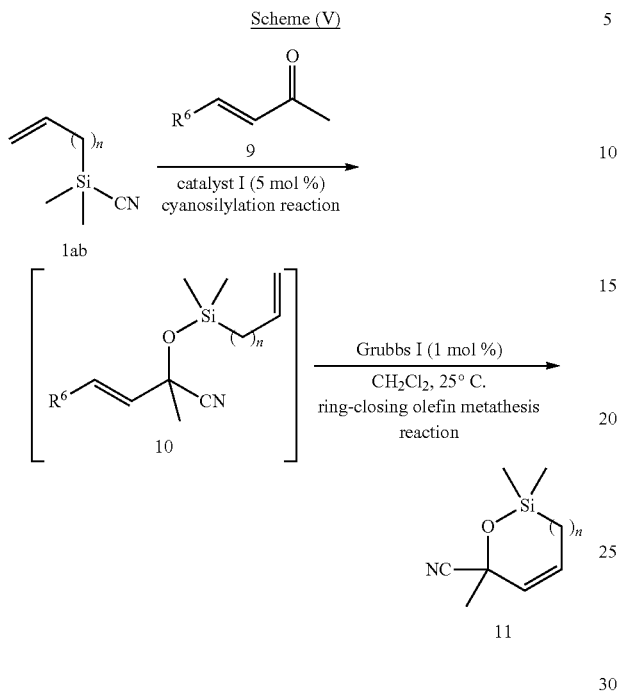

Scheme (V)

General procedure 9: the catalyst I (0.05 mmol), a raw material 9 (1.0 mmol) and a corresponding solvent (1 mL) were added into a dry Schlenk tube (25 mL). The mixture was added with 1ab (1.5 mmol) after being stirred at a corresponding temperature for 0.5 h. The progress of the reaction was monitored by TLC analysis. After the consumption of the raw material 9 was complete, crude product 10 was obtained by filtering the reaction mixture by 5 cm silica gel column, eluting with Et$_2$O, and removing solvent under reduced pressure. The crude product 10 was transferred to a dry Schlenk tube (25 mL) and dissolved with anhydrous CH$_2$Cl2 (2.0 mL), and added with catalyst Grubbs I (0.01 mmol) at 25° C. The progress of the reaction was monitored by TLC analysis. After the consumption of the 10 was complete, the desired product 11 as shown in Scheme (V) was obtained from the reaction mixture by column chromatography directly.

The specific experimental operations of the examples 244-255 are shown in general procedure 9. The specific reaction conditions and yield of each example are shown in Table 9.

TABLE 9

Specific reaction conditions and yields of the examples 244-255.

| Example | n | R$^6$ | Catalyst I | Product | Yield (%)/Ee (%) |
|---|---|---|---|---|---|
| 244 | 0 | Me | K$_2$CO$_3$ | 11a | 75/— |
| 245 | 1 | Me | K$_2$CO$_3$ | 11b | 73/— |
| 246 | 4 | Me | K$_2$CO$_3$ | 11c | 69/— |
| 247 | 1 | H | K$_2$CO$_3$ | 11b | 60/— |
| 248 | 1 | Et | K$_2$CO$_3$ | 11b | 70/— |
| 249 | 1 | Ph | K$_2$CO$_3$ | 11b | 78/— |
| 250 | 0 | Me | IC1 (R$^4$ = OEt) | 11a | 68/96 |
| 251 | 1 | Me | IC1 (R$^4$ = OEt) | 11b | 70/95 |

TABLE 9-continued

Specific reaction conditions and yields of the examples 244-255.

| Example | n | R$^6$ | Catalyst I | Product | Yield (%)/Ee (%) |
|---|---|---|---|---|---|
| 252 | 4 | Me | IC1 (R$^4$ = OEt) | 11c | 75/92 |
| 253 | 1 | H | IC1 (R$^4$ = OEt) | 11b | 60/90 |
| 254 | 1 | Et | IC1 (R$^4$ = OEt) | 11b | 77/96 |
| 255 | 1 | Ph | IC1 (R$^4$ = OEt) | 11b | 73/92 |

The characterizations of 11a-11c are as follows:

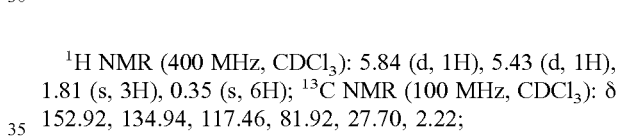

11a $^1$H NMR (400 MHz, CDCl$_3$): 5.84 (d, 1H), 5.43 (d, 1H), 1.81 (s, 3H), 0.35 (s, 6H); $^{13}$C NMR (100 MHz, CDCl$_3$): δ 152.92, 134.94, 117.46, 81.92, 27.70, 2.22;

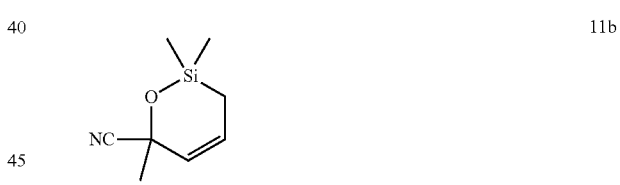

11b $^1$H NMR (400 MHz, CDCl$_3$): 5.68-5.61 (m, 2H), 2.03 (d, 2H), 1.87 (s, 3H), 0.33 (s, 6H); (s, 6H); $^{13}$C NMR (100 MHz, CDCl$_3$): δ 152.04, 136.84, 118.40, 81.92, 75.78, 27.40, 2.82;

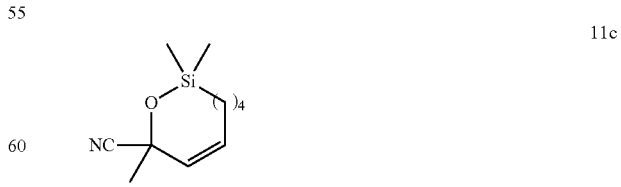

11c $^1$H NMR (400 MHz, CDCl$_3$): 5.67-5.60 (m, 2H), 2.03 (m, 2H), 1.87 (s, 3H), 1.44-1.30 (m, 6H), 0.35 (s, 6H); $^{13}$C NMR (100 MHz, CDCl$_3$): δ 137.26, 131.80, 119.50, 75.58, 30.97, 30.00, 29.38, 23.57, 15.78, 2.48.

10) Epoxy Ring-Opening Reaction/Functional Mass Transfer Reaction of Functionalized Silyl Cyanide 1aa (Table 10).

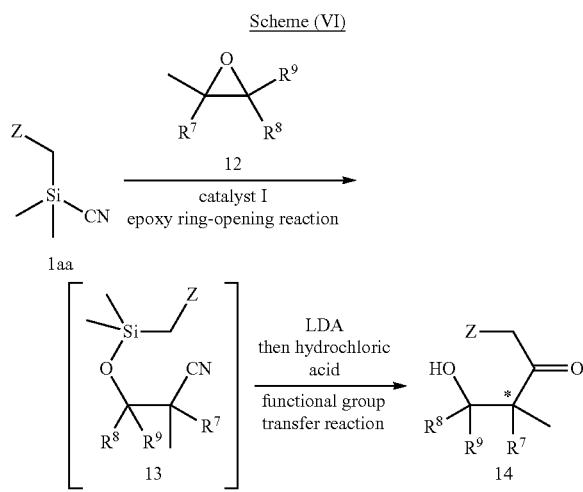

Scheme (VI)

General procedure 10: the catalyst I, a raw material 12 (1.0 mmol) and a corresponding solvent (1 mL) were added into a dry Schlenk tube (25 mL). The mixture was added with 1aa (1.5 mmol) after being stirred at a corresponding temperature for 0.5 h. The process of the reaction was monitored by TLC analysis. After the consumption of the raw material 12 was complete, crude product 13 was obtained by filtering the reaction mixture by 5 cm silica gel column, eluting with Et2O, and removing solvent under reduced pressure. The crude product 13 was transferred to a dry Schlenk tube (25 mL) and dissolved with anhydrous THF (4.0 mL). The resulting solution was stirred at −30° C. for 0.5 h, and then LDA (1.5 mmol) was added dropwise slowly. The progress of the reaction was monitored by TLC analysis. After the consumption of the 13 was complete, the reaction mixture was quenched by 5 mL hydrochloric acid (4 M), and then extracted three times by EtOAc. The desired product 14 as shown in Scheme (III) was obtained by combing the organic phase, rotary evaporating to remove the solvent and column chromatography.

The specific experimental operations of the examples 256-286 are referred to general procedure 10. The specific reaction conditions and yield of each example are shown in Table 10.

TABLE 10

Specific reaction conditions and yields of the examples 256-286

| Example | $R^7/R^8/R^9/Z$ | Catalyst I (mol %) | Solvent | T1 (° C.) | Product/Yield (%)/Ee (%) |
|---|---|---|---|---|---|
| 256 | Ph/Me/Me/Cl | $Na_2CO_3$ (5) | MeCN | 25 | 14a/63/— |
| 257 | Ph/Me/Me/Cl | $Li_2CO_3$ (5) | MeCN | 25 | 14a/64/— |
| 258 | Ph/Me/Me/Cl | $Na_2CO_3$ (5) | MeCN | 25 | 14a/70/— |
| 259 | Ph/Me/Me/Cl | CsOAc (25) | MeCN | 25 | 14a/63/— |
| 260 | Ph/Me/Me/Cl | $Et_3N$ (5) | MeCN | 25 | 14a/68/— |
| 261 | Ph/Me/Me/Cl | $Zn(OTf)_2$ (0.1) | MeCN | 25 | 14a/73/— |
| 262 | Ph/Me/Me/Cl | KI (10) | MeCN | 25 | 14a/66/— |
| 263 | Ph/Me/Me/Cl | $TiCl_4$ (0.5) | MeCN | 25 | 14a/65/— |
| 264 | Ph/Me/Me/Cl | $ZnI_2$ (0.5) | MeCN | 25 | 14a/65/— |
| 265 | Bn/Me/Me/Cl | $Na_2CO_3$ (5) | MeCN | 25 | 14b/71/— |
| 266 | $BnCH_2$/Me/Cl | $Na_2CO_3$ (5) | MeCN | 25 | 14c/75/— |
| 267 | $BnCH_2$/Me/Br | $Na_2CO_3$ (5) | MeCN | 25 | 14d/65/— |
| 268 | Et/allyl/allyl/Cl | $Na_2CO_3$ (5) | MeCN | 25 | 14e/65/— |
| 269 | Ph/Et/Et/Cl | $Na_2CO_3$ (5) | MeCN | 40 | 14f/68/— |
| 270 | Ph/Allyl/Allyl/Cl | $Na_2CO_3$ (5) | MeCN | 35 | 14g/66/— |
| 271 | Ph/H/H/Cl | $Na_2CO_3$ (5) | MeCN | 25 | 14h/38/— |
| 272 | Ph/Et/Me/Cl | $Na_2CO_3$ (5) | MeCN | 25 | 14i/33/— |
| 273 | Ph/Allyl/Me/Cl | $Na_2CO_3$ (5) | MeCN | 25 | 14j/35/— |
| 274 | Ph/Me/Me/Cl | IC1 ($R^4$ = Me) | $Et_2O$ | 25 | 14a/33/87 |
| 275 | Ph/Me/Me/Cl | IC1 ($R^4$ = OEt) | $Et_2O$ | −30 | 14a/40/92 |
| 276 | Ph/Me/Me/Cl | IC1 ($R^4$ = H) | $Et_2O$ | −30 | 14a/31/85 |
| 277 | Ph/Me/Me/Cl | IC1 ($R^4$ = Ot-Bu) | $Et_2O$ | −30 | 14a/37/90 |
| 278 | Bn/Me/Me/Cl | IC1 ($R^4$ = OEt) | $Et_2O$ | −30 | 14b/38/85 |

TABLE 10-continued

Specific reaction conditions and yields of the examples 256-286

| Example | $R^7/R^8/R^9$/Z | Catalyst I (mol %) | Solvent | T1 (° C.) | Product/Yield (%)/Ee (%) |
|---|---|---|---|---|---|
| 279 | BnCH$_2$/Me/Cl | IC1 ($R^4$ = OEt) | Et$_2$O | −30 | 14c/42/80 |
| 280 | BnCH$_2$/Me/Br | IC1 ($R^4$ = OEt) | Et$_2$O | −30 | 14d/35/82 |
| 281 | Et/allyl/allyl/Cl | IC1 ($R^4$ = OEt) | Et$_2$O | −30 | 14e/35/75 |
| 282 | Ph/Et/Et/Cl | IC1 ($R^4$ = OEt) | Et$_2$O | −30 | 14f/35/73 |
| 283 | Ph/Allyl/Allyl/Cl | IC1 ($R^4$ = OEt) | Et$_2$O | −30 | 14g/36/70 |
| 284 | Ph/H/H/Cl | IC1 ($R^4$ = OEt) | Et$_2$O | −30 | 14h/28/67 |
| 285 | Ph/Et/Me/Cl | IC1 ($R^4$ = OEt) | Et$_2$O | −30 | 14i/39/80 |
| 286 | Ph/Allyl/Me/Cl | IC1 ($R^4$ = OEt) | Et$_2$O | −30 | 14j/38/85 |

The characterizations of compounds 14a-14j are as follows:

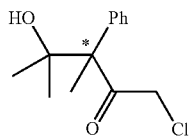

14a $^1$H NMR (400 MHz, CDCl$_3$): 7.50-7.38 (m, 2H), 7.22-7.14 (m, 3H), 4.42 (dd, 2H), 3.7 (s, 1H), 3.12 (s, br, 1H), 1.67 (s, 3H), 1.26 (s, 3H); $^{13}$C NMR (100 MHz, CDCl$_3$): δ 197.94, 139.14, 131.28, 128.97, 127.91, 74.88, 70.58, 50.52, 26.81;

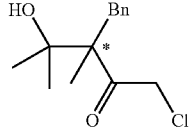

14b $^1$H NMR (400 MHz, CDCl$_3$): 7.40-7.35 (m, 2H), 7.29-7.17 (m, 3H), 4.52 (dd, 2H), 3.12 (s, br, 1H), 3.09 (dd, 1H), 2.84-2.80 (m, 2H), 1.67 (s, 3H), 1.26 (s, 3H); $^{13}$C NMR (100 MHz, CDCl$_3$): δ 202.81, 137.81, 129.07, 128.73, 127.06, 75.93, 63.52, 49.53, 28.58, 27.87;

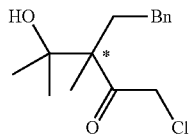

14c $^1$H NMR (400 MHz, CDCl$_3$): 7.42-7.30 (m, 2H), 7.28-7.15 (m, 3H), 4.54 (dd, 2H), 3.15 (s, br, 1H), 2.55 (t, 2H), 2.40 (t, 1H), 1.86 (1, 2H), 1.67 (s, 3H), 1.25 (s, 6H); $^{13}$C NMR (100 MHz, CDCl$_3$): δ 207.26, 141.62, 129.07, 128.37, 126.35, 76.10, 57.27, 49.53, 35.95, 28.58, 25.75;

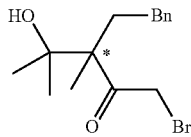

14d $^1$H NMR (400 MHz, CDCl$_3$): 7.44-7.31 (m, 2H), 7.27-7.14 (m, 3H), 4.46 (dd, 2H), 3.18 (s, br, 1H), 2.56 (t, 2H), 2.43 (t, 1H), 1.85 (1, 2H), 1.67 (s, 3H), 1.27 (s, 6H); $^{13}$C NMR (100 MHz, CDCl$_3$): δ 206.07, 141.62, 129.07, 128.37, 126.35, 76.10, 60.50, 38.06, 35.95, 28.58, 25.75;

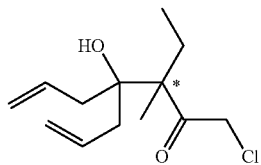

14e $^1$H NMR (400 MHz, CDCl$_3$): 5.94-5.81 (m, 2H), 5.17-4.94 (m, 4H), 4.47 (dd, 2H), 3.58 (s, br, 1H), 2.58 (q, 1H), 2.13 (d, 2H), 1.67 (s, 3H), 1.15 (d, 3H); $^{13}$C NMR (100 MHz, CDCl$_3$): δ 198.64, 133.18, 119.40, 73.02, 52.25, 48.49, 47.30, 10.56;

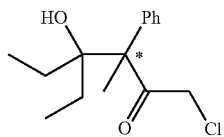

14f $^1$H NMR (400 MHz, CDCl$_3$): 7.47-7.39 (m, 2H), 7.32-7.14 (m, 3H), 4.41 (dd, 2H), 3.73 (s, 1H), 3.15 (s, br, 1H), 1.67 (s, 3H), 1.55 (q, 4H), 0.96 (t, 6H); $^{13}$C NMR (100 MHz, CDCl$_3$): δ 198.74, 138.38, 131.51, 128.96, 127.79, 72.56, 65.98, 50.52, 31.54, 7.62;

14g

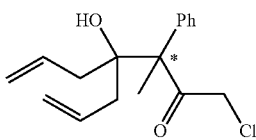

¹H NMR (400 MHz, CDCl₃): 7.47-7.39 (m, 2H), 7.32-7.14 (m, 3H), 5.94-5.81 (m, 2H), 5.17-4.94 (m, 4H), 4.42 (dd, 2H), 3.73 (s, 1H), 3.15 (s, br, 1H), 2.05 (d, 4H), 1.67 (s, 3H); ¹³C NMR (100 MHz, CDCl₃): δ 198.74, 138.38, 133.18, 131.51, 128.96, 127.79, 119.40, 72.78, 69.84, 50.52, 44.59;

14h

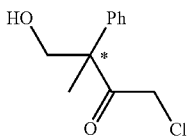

¹H NMR (400 MHz, CDCl₃): 7.45-7.33 (m, 2H), 7.27-7.14 (m, 3H), 4.45 (dd, 2H), 4.23 (dd, 1H), 3.95 (dd, 1H), 3.65 (s, br, 1H), 1.67 (s, 3H); ¹³C NMR (100 MHz, CDCl₃): δ 189.78, 137.59, 130.52, 128.69, 128.24, 66.24, 55.33, 51.14;

14i

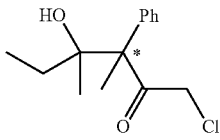

¹H NMR (400 MHz, CDCl₃): 7.46-7.38 (m, 2H), 7.33-7.15 (m, 3H), 4.41 (dd, 2H), 3.74 (s, 1H), 3.45 (s, br, 1H), 1.67 (s, 3H), 1.53 (q, 2H), 1.23 (s, 3H), 0.95 (t, 3H); ¹³C NMR (100 MHz, CDCl₃): δ 199.25, 138.12, 131.06, 128.93, 127.66, 72.93, 65.48, 50.52, 33.39, 23.22, 7.41;

14j

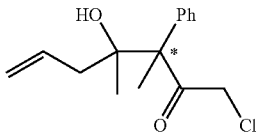

¹H NMR (400 MHz, CDCl₃): 7.47-7.39 (m, 2H), 7.32-7.14 (m, 3H), 5.90-5.80 (m, 1H), 5.19-4.92 (m, 2H), 4.45 (dd, 2H), 3.75 (s, 1H), 3.35 (s, br, 1H), 2.05 (dd, 1H); 1.95 (dd, 1H), 1.67 (s, 3H), 1.36 (s, 3H); ¹³C NMR (100 MHz, CDCl₃): δ 199.25, 138.12, 133.16, 131.06, 128.93, 127.66, 119.35, 74.20, 68.20, 50.52, 45.79, 24.04.

It will be apparent to those skilled in the art that modifications and variations can be made without departing from the scope and spirit disclosed by the appended claims of the present disclosure, and such modifications and variations all fall in the protection extent of the claims of the present disclosure.

What is claimed is:

1. A functionalized silyl cyanide having the following formula (1):

Formula (1)

wherein,

FG is selected from F, Cl, Br, I, CHF₂, CHCl₂, —CH₂CH=CR₂, —CH=CR₂ and —C≡CR; wherein, —CH₂CH=CR₂, —CH=CR₂ and —C≡CR are functional groups having unsaturated carbon-carbon bond, wherein, R is H, Me;

R¹ is Me, Et;

n=1-5;

wherein when n=1 and each R¹ is Me, FG is not —CH=CH₂.

2. A compound, having the following structural Formula (7),

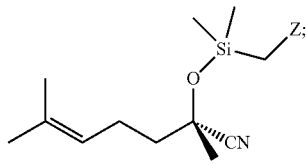

Formula (7)

wherein, Z is Cl, Br.

* * * * *